(12) United States Patent
Tsugo

(10) Patent No.: US 10,446,270 B2
(45) Date of Patent: Oct. 15, 2019

(54) DATA OUTPUT DEVICE AND METHOD, AND NON-TRANSITORY COMPUTER READABLE MEDIUM

(71) Applicant: FUJIFILM Corporation, Tokyo (JP)

(72) Inventor: Akinari Tsugo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 350 days.

(21) Appl. No.: 15/280,366

(22) Filed: Sep. 29, 2016

(65) Prior Publication Data
US 2017/0017764 A1 Jan. 19, 2017

Related U.S. Application Data

(63) Continuation of application No. PCT/JP2015/057933, filed on Mar. 17, 2015.

(30) Foreign Application Priority Data

Mar. 31, 2014 (JP) ................................ 2014-074277

(51) Int. Cl.
A61B 5/00 (2006.01)
G06F 19/00 (2018.01)
(Continued)

(52) U.S. Cl.
CPC .............. G16H 40/63 (2018.01); A61B 5/742 (2013.01); G06F 19/00 (2013.01); G06Q 10/10 (2013.01); G06Q 50/24 (2013.01); G16H 10/60 (2018.01)

(58) Field of Classification Search
CPC ........ A61B 5/742; G06F 19/00; G06Q 10/10; G06Q 50/24; G16H 10/60; G16H 40/63
See application file for complete search history.

(56) References Cited

U.S. PATENT DOCUMENTS 8,585,593 B2 * 11/2013 Kovatchev ............. A61B 5/024
600/365
2008/0001735 A1 * 1/2008 Tran .................... G06F 19/3418
340/539.22

(Continued)

FOREIGN PATENT DOCUMENTS

JP 2012-63997 A 3/2012
JP 2013-841082 A 5/2013

OTHER PUBLICATIONS

English Translation of International Preliminary Report on Patentability (including PCT/IB/373 and PC/ISA/237) for PCT/JP2015/057933, dated Oct. 4, 2016.

(Continued)

Primary Examiner — Sing-Wai Wu
(74) Attorney, Agent, or Firm — Birch, Stewart, Kolasch & Birch, LLP

(57) ABSTRACT

A data output device, a data output method, and a data output program capable of allowing a causal relationship in a plurality of items of time-series data to be simply recognized are provided.

A data distribution server receives a distribution request from a client terminal, and generates a data display screen which is displayed by the client terminal. The data display screen includes a first display area in which time-series data indicating a transition of a state of a patient or content of medical care performed on the patient is displayed in a graph. In the first display area, association indicators which associate one arbitrary point of each of the plurality of pieces of time-series data can be assigned and displayed.

18 Claims, 29 Drawing Sheets

(51) Int. Cl.
*G16H 40/63* (2018.01)
*G16H 10/60* (2018.01)
*G06Q 50/24* (2012.01)
*G06Q 10/10* (2012.01)

(56) References Cited

U.S. PATENT DOCUMENTS

| | | |
|---|---|---|
| 2008/0145830 A1* | 6/2008 | Huang .................... G09B 9/00 |
| | | 434/336 |
| 2009/0005703 A1 | 1/2009 | Fasciano |
| 2009/0131805 A1 | 5/2009 | O'Brien et al. |
| 2010/0057043 A1 | 3/2010 | Kovatchev et al. |

OTHER PUBLICATIONS

Chinese Office Action dated Mar. 30, 2018, issued in corresponding Chinese patent application No. 201580017926.4.
International Search Report for PCT/JP2015/057933 (PCT/ISA/210) dated Jun. 16, 2015.
Written Opinion of the International Searching Authority for PCT/JP2015/057933 (PCT/ISA/237) dated Jun. 16, 2015.
Chinese Office Action dated Dec. 3, 2018, for corresponding Chinese Patent Application No. 201580017926.4, with English translation.
Chinese Office Action and Search Report for corresponding Chinese Application No. 201580017926.4, dated May 14, 2019, with English translation of the Office Action.

* cited by examiner

DATA OUTPUT DEVICE AND METHOD, AND NON-TRANSITORY COMPUTER READABLE MEDIUM

CROSS-REFERENCE TO RELATED APPLICATION

This application is a Continuation of PCT International Application PCT/JP2015/057933 filed on 17 Mar. 2015, which claims priority under 35 USC 119(a) from Japanese Patent Application No. 2014-074277 filed on 31 Mar. 2014. The above application is hereby expressly incorporated by reference, in its entirety, into the present application.

BACKGROUND OF THE INVENTION

1. Field of the Invention

The present invention relates to a data output device and a data output method that output time-series data regarding medical care, and a non-transitory computer readable medium.

2. Description of the Related Art

In recent years, various medical care information acquired in medical care of a patient has been stored and managed as electronic data using a computer system. In the medical care information, for example, measured values of vital signs such as a heart rate, a pulse rate, blood pressure, and body temperature, inspection values in specimen inspection such as blood inspection, and data regarding treatment such as a name of an administered drug and a dosage are included. In medical care, it is important to recognize a transition of a condition of a patient such as a change over time in body temperature or blood pressure or a change in inspection values of a plurality of inspections performed in different periods of time, or recognize content of treatment or therapy in time series. Therefore, a display device that displays, in a graph form, time-series data in which a measured value or an inspection value of a vital sign is recorded in time series is known (see, for example, JP2012-063997A and JP2013-084082A).

In a display device disclosed in JP2012-063997A, in a system that displays a plurality of pieces of time-series data for each of action items such as medication, inspection, and injection, "action item", "time width" of start time and end time associated with each action item, and "numerical value" associated with the action item can be collected and stored as events, and the action items between the events can be associated with each other, as described in paragraphs 0028 to 0031.

A display device in JP2013-084082A can display time-series data of inspection values in the form of a graph, and can display a plurality of pieces of time-series data, as in JP2012-063997A. For each item of the time-series data, an indicator can be assigned at any designated position in the time-series data. Further, a comment regarding medical examination, therapy, or the like, which is related to an inspection value to which the indicator has been assigned, can be recorded in association with the indicator.

In the event that content of a treatment or a therapy for a patient is determined, it is necessary to examine time-series data such as inspection values in detail in order to accurately recognize a state of a patient. Particularly, it is important to recognize the causal relationship between a plurality of pieces of time-series data. For example, in a case in which the blood pressure decreases as a side effect due to medication, a result of an unexpected decrease in blood pressure occurs due to a cause of medication, the causal relationship is recorded and stored, and the causal relationship is displayed and confirmed at the time of the next medical care. Accordingly, content of next treatment or therapy can be appropriately determined.

A causal relationship may be recognized, for example, in the following procedure using a function of displaying a plurality of items of time-series data described in JP2012-063997A or JP2013-084082A. First, a time, a period, or an interval at which medication is performed is displayed in one piece of time-series data, and a change over time in blood pressure is displayed in another piece of time-series data. Through work of collating a plurality of pieces of such time-series data, a timing of medication as a cause or a timing at which an unexpected side effect such as a decrease in blood pressure has been expressed as a result is obtained, and a causal relationship between the medication and the decrease in blood pressure can be ascertained.

In the display devices described in JP2012-063997A and JP2013-084082A, since a function of recording a causal relationship is insufficient as shown below, there is a problem in that identifying the causal relationship needs to be repeated again and the causal relationship cannot be simply looked back in the event that previous content of medical care is looked back.

In JP2012-063997, there is a function of associating a plurality of action items (events) with each other. However, since one event is defined by a "time width", any positions in the time-series data defined by the "time width" cannot be associated with each other. Therefore, in a case in which any points in time in the time-series data are important points in time representing a cause or a result, the causal relationship between both cannot be recorded.

For example, since data of a vital sign such as blood pressure is often regularly measured over a long period of time and a "time width" is a long period of time, a display of the event is in a long period of time in time-series. Thus, in a case in which injection is performed within a long measurement period of the blood pressure, the injection and the time-series data of blood pressure for a long period of time can be associated with each other in a technology of JP2012-063997A. Accordingly, a causal relationship between the injection and the blood pressure likely to be influenced by the injection can be focused upon. However, since such a degree of causal relationship is content of general knowledge that can be easily estimated in advance, this is likely not to be information useful in actual medical care for determining a specific medical care plan of individual patients. Further, since a specific causal relationship cannot be simply recognized even in the event that the event is looked back later, efficiency of medical care cannot be improved. It is necessary for a correspondence between a specific change point in time in the time-series data of a measured value recorded in blood pressure measurement over a long period of time and a point in time of injection to be able to be recognized for useful information in actual medical care and efficient subsequent look-back.

Further, in another example, in a case in which a relationship between medication and an inspection result is considered, a time taken for an effect to be expressed, of course, is different due to, for example, dispositions of individuals in the medication, and accordingly, an notable point in time at which the effect for an inspection result is determined changes on an individual basis. That is, even in the event that a technology of JP2012-063997A is applied in a case in which medication is performed for a long period of time as in rheumatism and the same inspection value is monitored for a long period of time, a different notable point in time for each patient cannot be easily recognized. Accordingly, the efficiency of diagnosis cannot be increased. Assuming that an effect of the medication is expressed, a dosage may gradually decrease, but in JP2012-063997A, a correspondence between a point in time at which the dosage is changed and how the inspection value changes as a result according to the change cannot be recorded.

On the other hand, in JP2013-084082A, an indicator with a comment can be assigned at any position in the time-series data, but association of a plurality of pieces of time-series data cannot be recognized. Accordingly, for example, in a case in which a cause and a result are distributed in a plurality of pieces of time-series data, a causal relationship cannot be recorded. Further, neither JP2012-063997A nor JP2013-084082A describes that a display is performed so that a causal relationship between items of data at a specific point in time can be recorded and then looked back.

Thus, in the display devices described in JP2013-084082A and JP2012-063997A, since a function of recording and confirming a causal relationship is insufficient, there is a problem in that the causal relationship cannot be simply recognized in the event that previous content of medical care is looked back.

SUMMARY OF THE INVENTION

An object of the present invention is to provide a data output device capable of allowing a causal relationship in a plurality of items of time-series data to be simply recognized.

In order to solve the above problem, a data output device of the present invention is a data output device for displaying time-series data indicating at least one of a transition of a condition of a patient or content of medical care performed on the patient, and comprises a screen data generation unit, an association instruction reception unit, and an association processing unit. The screen data generation unit generates screen data of a data display screen for displaying at least two items of time-series data including first time-series data and second time-series data. The association instruction reception unit receives an association instruction to associate an arbitrary first designated position in the first time-series data with an arbitrary second designated position in the second time-series data. The association processing unit assigns an association indicator indicating that the first designated position and the second designated position are associated with each other, in the data display screen, based on the association instruction.

It is preferable for the association processing unit to store association information indicating that the first designated position and the second designated position are associated with each other in a storage unit.

It is preferable for the association indicator to include a first indicator assigned at the first designated position, and a second indicator assigned at the second designated position.

It is preferable for at least one of the first designated position or the second designated position to be able to be designated as a plurality of positions.

It is preferable for the association processing unit to store information on the first designated position in the first time-series data, information on the second designated position in the second time-series data, and the association information, as one piece of set information, in the storage unit.

It is preferable for the set information to include causal relationship information indicating that one of the information on the first designated position and the information on the second designated position is a cause, and the other is a result.

It is preferable for the association processing unit to be capable of adding an input comment to the set information.

It is preferable for the comment to be displayed in the data display screen in addition to the association indicator or as the association indicator.

It is preferable for the data display screen to include a first display area for displaying the first time-series data and the second time-series data, and a list display area for displaying a plurality of pieces of set information as a list.

It is preferable for the list display area to be capable of displaying the comment included in the set information.

It is preferable that in a case in which one piece of set information in the list display area is selected, the association indicator corresponding to the selected set information is displayed to be distinguishable in the first display area.

It is preferable that in a case in which one association indicator in the first display area is selected, the set information corresponding to the selected association indicator is displayed to be identifiable in the list display area.

It is preferable for the data display screen to further include a second display area for displaying a time axis at a relatively longer time scale than that of the first display area. A corresponding indicator indicating that there is the association indicator is displayed at a corresponding position corresponding to a period from the first designated position to the second designated position in the time axis in the second display area.

It is preferable that in a case in which there are a plurality of sets of one piece of set information in the list display area and one corresponding indicator in the second display area corresponding to the set information, each set is displayed to be identifiable.

It is preferable that an order of display of a plurality of pieces of set information is able to be changed in the list display area.

It is preferable that the order of display of the set information is any one of an order of creation of the set information and an order of access to the set information.

It is preferable for the data output device to further comprise a grouping unit that groups one or more pieces of set information.

It is preferable that in a case in which the data display screen is used for a conference in which a medical care plan for a patient is examined by a plurality of persons, the grouping unit is capable of collecting and storing a plurality of pieces of set information created or accessed during a period of the conference, in one group using one conference as a unit.

Further, a data output method of the present invention is a data output method for displaying time-series data indicating at least one of a transition of a condition of a patient or content of medical care performed on the patient on a display unit, and comprises a screen data generation step, an association instruction reception step, and an association processing step. The screen data generation step includes generating screen data of a data display screen for displaying at least two items of time-series data including first time-series data and second time-series data. The association instruction reception step includes receiving an association instruction to associate an arbitrary first designated position in the first time-series data with an arbitrary second designated position in the second time-series data. The association processing step includes assigning an association indicator indicating that the first designated position and the second designated position are associated with each other, in the data display screen, based on the association instruction.

A non-transitory computer readable medium according to the invention stores a computer-executable program enabling execution of computer instructions to perform operations for displaying time-series data indicating at least one of a transition of a condition of a patient or content of medical care performed on the patient on a display unit. The operations include generating screen data of a data display screen for displaying at least two items of time-series data including first time-series data and second time-series data, receiving an association instruction to associate an arbitrary first designated position in the first time-series data with an arbitrary second designated position in the second time-series data, and assigning an association indicator indicating that the first designated position and the second designated position are associated with each other, in the data display screen, based on the association instruction.

According to the present invention, it is possible to simply recognize a causal relationship in the first and second time-series data since the screen data for displaying the first time-series data and the second time-series data indicating the transition of a condition of a patient or content of medical care performed on the patient is generated, the association instruction to associate the arbitrary first and second designated positions designated in the respective items of time-series data is received, and the association indicator indicating that the first designated position and the second designated position are associated with each other is displayed on the screen.

BRIEF DESCRIPTION OF THE DRAWINGS

FIG. 5 is a block diagram illustrating an electrical configuration of a computer used for a data distribution server or the like.

DESCRIPTION OF THE PREFERRED EMBODIMENTS

First Embodiment

Figure 1:
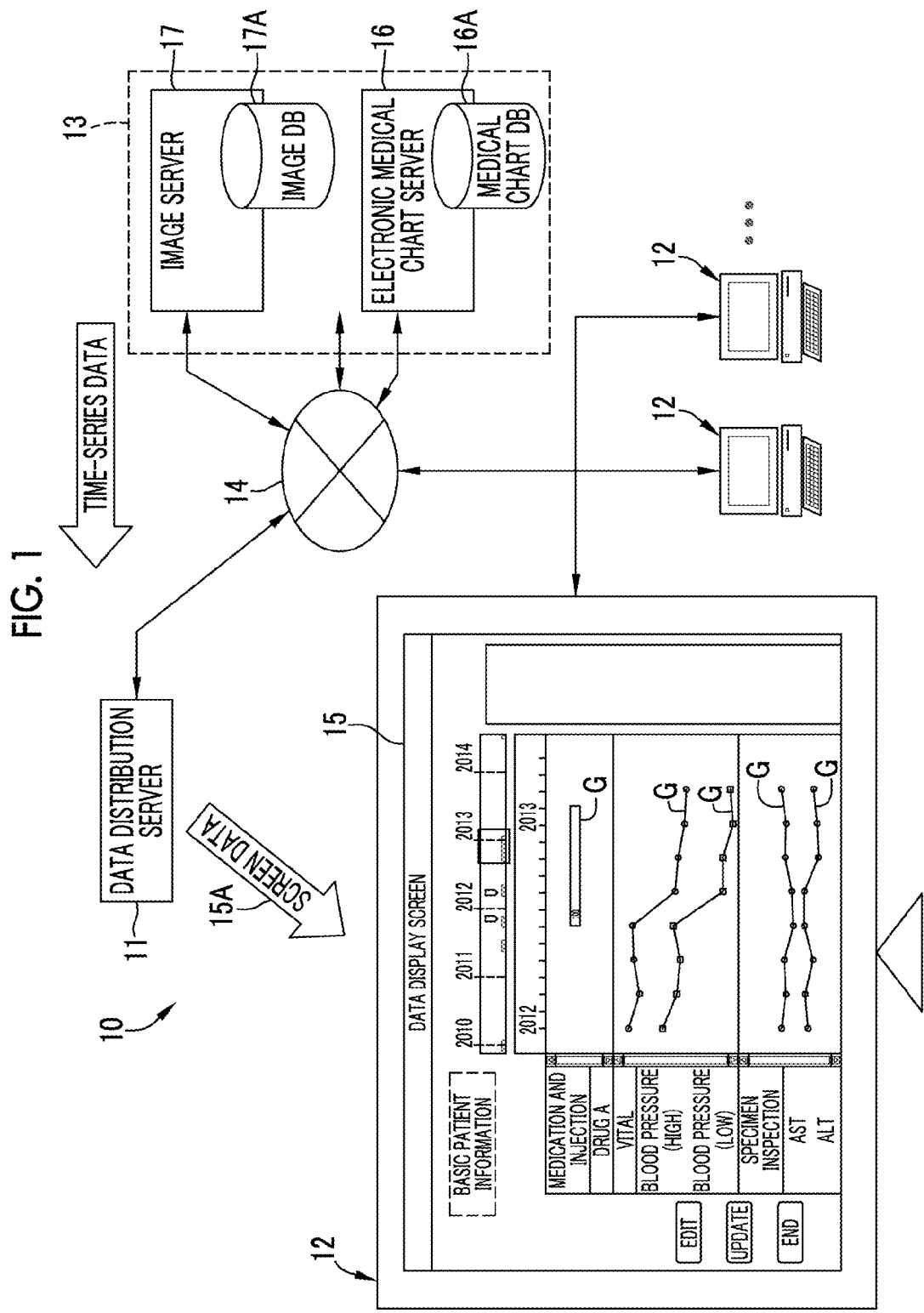
FIG. 1 is an illustrative diagram illustrating a configuration of a medical information management system in which the present invention is embodied.

A medical information system 10 illustrated in FIG. 1 is a computer system that is used to manage information on medical care at a medical facility such as a hospital. This medical information system 10 includes a data distribution server 11, a client terminal 12, a server group 13, and a network 14 that connects the components so that the components can communicate with each other. In the server group 13, an electronic medical chart server 16, and an image server 17 are included. The network 14 is, for example, a local area network (LAN) that is laid in a hospital.

The client terminal 12 is a terminal that is installed in respective medical care departments such as an internal medicine, a surgery, an otolaryngology, and ophthalmology and is operated, for example, by a doctor in the medical care department. The client terminal 12 has a function of accessing the electronic medical chart server 16 and inputting and viewing electronic medical charts. Medical care information including a record of medical examination such as medical interview, inspection, or diagnosis, and a record of treatment such as treatment or surgery are input to the electronic medical chart. Further, the client terminal 12 has a function of accessing the image server 17 and viewing inspection images such as X-ray images.

Further, the client terminal 12 has a function of accessing the data distribution server 11 and viewing a data display screen 15 on which time-series data in which an inspection value or a measured value regarding a medical care of a patient is recorded in time series is displayed. In the data display screen 15, the time-series data is displayed, for example, in the form of a graph G. The client terminal 12 receives screen data 15A of the data display screen 15 from the data distribution server 11, and reproduces and displays the data display screen 15 on the basis of the screen data 15A.

The data distribution server 11 acquires the time-series data from the electronic medical chart server 16 or the image server 17 on the basis of a distribution request from the client terminal 12, generates the screen data 15A on the basis of the acquired time-series data, and distributes the generated screen data 15A to the client terminal 12 that is a request source. The data distribution server 11 is a data output device of the present invention that performs data distribution, which is one form of data output regarding the time-series data.

The electronic medical chart server 16 includes an electronic medical chart database 16A (hereinafter referred to as a medical chart DB) in which the electronic medical chart is stored. The image server 17 has an image DB 17A in which a plurality of inspection images are stored, and is a so-called Picture Archiving and Communication System (PACS) server. The chart DB 16A and the image DB 17A are databases in which search can be performed based on a keyword, such as a patient ID.

Figure 2:
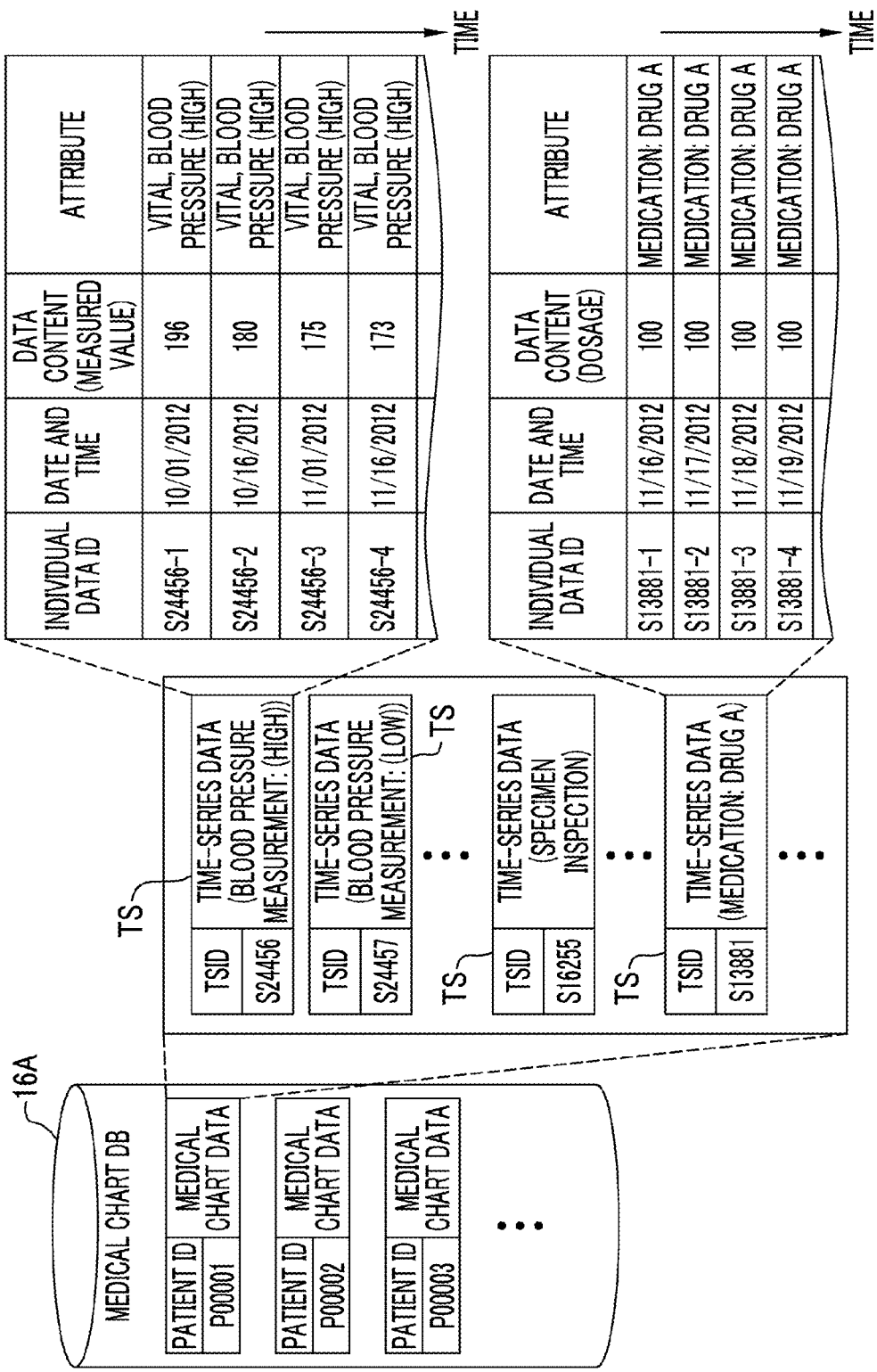
FIG. 2 is an illustrative diagram illustrating an example of time-series data recorded in an electronic medical chart.

As illustrated in FIG. 2, in the chart DB 16A, a patient ID (P0001, P00002 • • •) is assigned to the medical chart data in which medical care information on the patient is recorded, and stored in units of patients. The medical chart data includes time-series data TS, in addition to basic patient information such as patient s name, date of birth, gender, and patient ID.

The time-series data TS is data indicating a transition of a condition of a patient and content of medical care performed on the patient. The transition of a condition of a patient refers to, for example, a temporal change in a measured value of a vital sign such as a heart rate, a pulse, blood pressure, or body temperature of a patient, or an inspection value of clinical inspection performed on a patient. The clinical inspection includes specimen inspection such as blood inspection or biochemical inspection, and physiological inspection such as electroencephalographic inspection. Time-series data indicating the state transition of the patient is a data series of a plurality of measured values or inspection values acquired over time. Content of medical care performed on the patient includes content of therapy such as medication, surgery, or treatment, or content of medical interview. Time-series data indicating the content of the medical care performed on the patient is data series indicating content of a plurality of medical cares performed over time.

The time-series data TS is, typically, data series including a plurality of pieces of individual data acquired in time series for each of the same medical care items, such as blood pressure measurement and medication, as elements. As shown in this example, assuming that time-series data TS is time-series data TS of the blood pressure measurement, a plurality of measurement values for which measurement date are different constitutes a plurality of pieces of individual data as an element of the time-series data TS. From the time-series data TS of the blood pressure measurement, it is possible to confirm a change over time in the patient's blood pressure. In this example, the time-series data TS of the blood pressure measurement is divided into blood pressure (high) and blood pressure (lower), which are recorded as one item of time-series data TS.

In the time-series data TS of medication, in a case in which the same drug is divided and administered in a plurality of times for a period of time, a dosage of each time constitutes a plurality of pieces of individual data as an element of the time-series data TS. Since the individual data of the medication in this example is recorded continuously for several days from Nov. 16, 2012 and the dosage of each individual data is the same amount ("100"), it can be confirmed from the time-series data TS of the medication that the same amount of drug A is administered to a patient once daily for several days.

A record of one piece of individual data includes, for example, data items: an individual data ID, date and time, data content (for example, measured value, dosage, or inspection data), and attribute. Information on the date and time is measurement date and time in the case of the measured value, inspection date and time in the case of the inspection value, and date and time in the event that medication has been performed or date and time of prescription in the case of the dosage. In a case in which the individual data is recorded a plurality of times a day, time information is also necessary so as to distinguish the respective items of individual data from one another, but in a case in which an acquisition frequency of the individual data is smaller than or equal to once per day, date information may be sufficient. The individual data ID is identification information that is assigned to each item of the individual data so as to specify the individual data. In this example, the individual data ID is provided as an independent data item separate from the date and time information, but since the individual data ID may specify the individual data, information on the date and time can be used as the individual data ID.

Further, since the medication may require a period until effects of the medication are expressed, for example, medication (taking a drug) over a predetermined period such as "taking drug by a predetermined amount in one day is continued for five days" may be instructed as one prescription. In this case, data of a prescription unit indicating content (a drug taking period and a dosage) of one prescription may be used as individual data. Date and time of this individual data is, for example, be prescription date and time.

The attribute is information assigned to classify data, and is information indicating a type of individual data. The attribute can also be used as a keyword for searching for the individual data. Further, since the individual data is a data element of time-series data, the individual data has a meaning as information indicating a type of time-series data. Examples of the attribute include a name of the individual data, a category to which the individual data belongs, and a name of a medical care item corresponding to the individual data. In this example, as an attribute of individual data of blood pressure, a name of a measured value of "blood pressure (high)" is assigned, and a category "vital" is assigned since the blood pressure is one of vital signs. Further, since the measured value of the blood pressure is a numerical value, a type of data "numerical value data" can be assigned as an attribute or a category "measured value" distinguished from the "inspection value" can be assigned as an attribute. Further, a name "blood pressure measurement" of the medical care item can be assigned.

In the time-series data TS of medication, a name "medication" of the medical care item or a drug name "drug A" is assigned in the attribute. Further, as an attributes of medication, an administration method such as injection or taking may be assigned. The attribute may be automatically assigned according to content of input data by the electronic medical chart server 16, or may be assigned by manual input.

Further, content of medical interview is included in content of the medical care, in addition to content of treatment such as medication, but in the case of the medical interview, a medical interview record for each medical interview becomes individual data. A series of the individual data of the medical interview that is acquired in time series at different timings becomes time-series data of the medical interview.

IDs for identifying respective pieces of time-series data TS ("TSID") such as "S24456" and "S24457" are assigned to the respective pieces of time-series data TS. Therefore, using the patient IDs, the TSIDs, and the individual data IDs, the medical chart data, the time-series data TS within the medical chart data, and the individual data within the time-series data TS can be specified and searched for.

Figure 3:
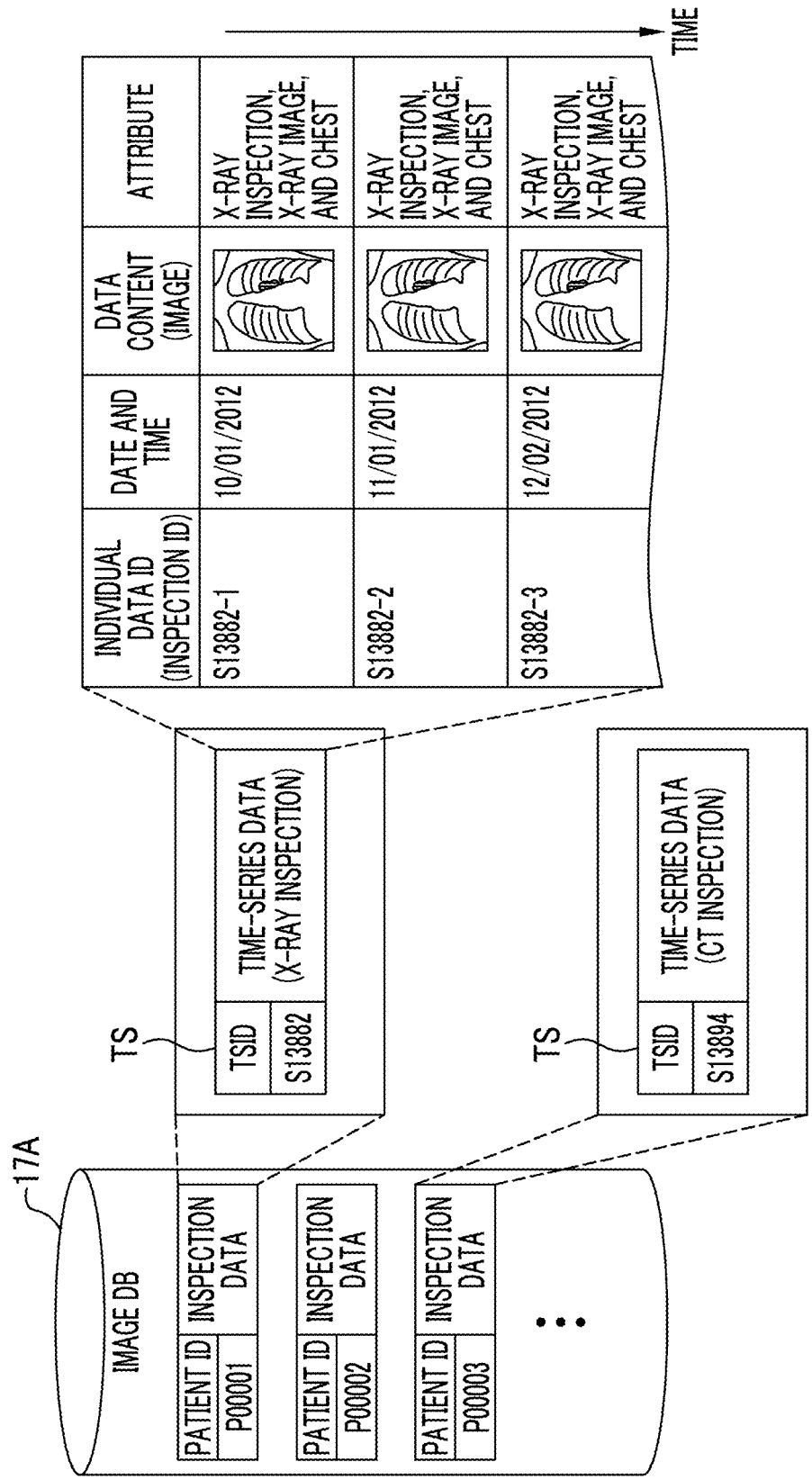
FIG. 3 is an illustrative diagram illustrating an example of time-series data recorded in an image server.

As illustrated in FIG. 3, inspection data including a plurality of inspection images captured in an image inspection such as an X-ray inspection or a CT inspection is stored in the image DB 17A. A patient ID is assigned to the inspection image, and the inspection image can be searched for using the patients ID. The image inspection may also be performed a plurality of times in medical care of one patient, as in a case in which progress observation is performed, and in this case, time-series data TS of the image inspection is acquired.

In the time-series data TS of the image inspection, the inspection image obtained by one image inspection becomes individual data. As an individual data ID, for example, an inspection ID is used. Since a plurality of tomographic images are acquired in one inspection in the case of the CT inspection, one piece of individual data includes a plurality of tomographic images. In the case of the X-ray inspection using a general X-ray imaging apparatus, since the number of X-ray images acquired in one inspection may be 1 or may be plural, the number of X-ray images in one piece of individual data may be 1 or may be plural. In an attribute of the individual data of the X-ray inspection, for example, information such as "X-ray inspection" indicating a type of inspection, "X-ray image" that is a type of image, and "chest" indicating an imaged part is assigned.

Figure 4:
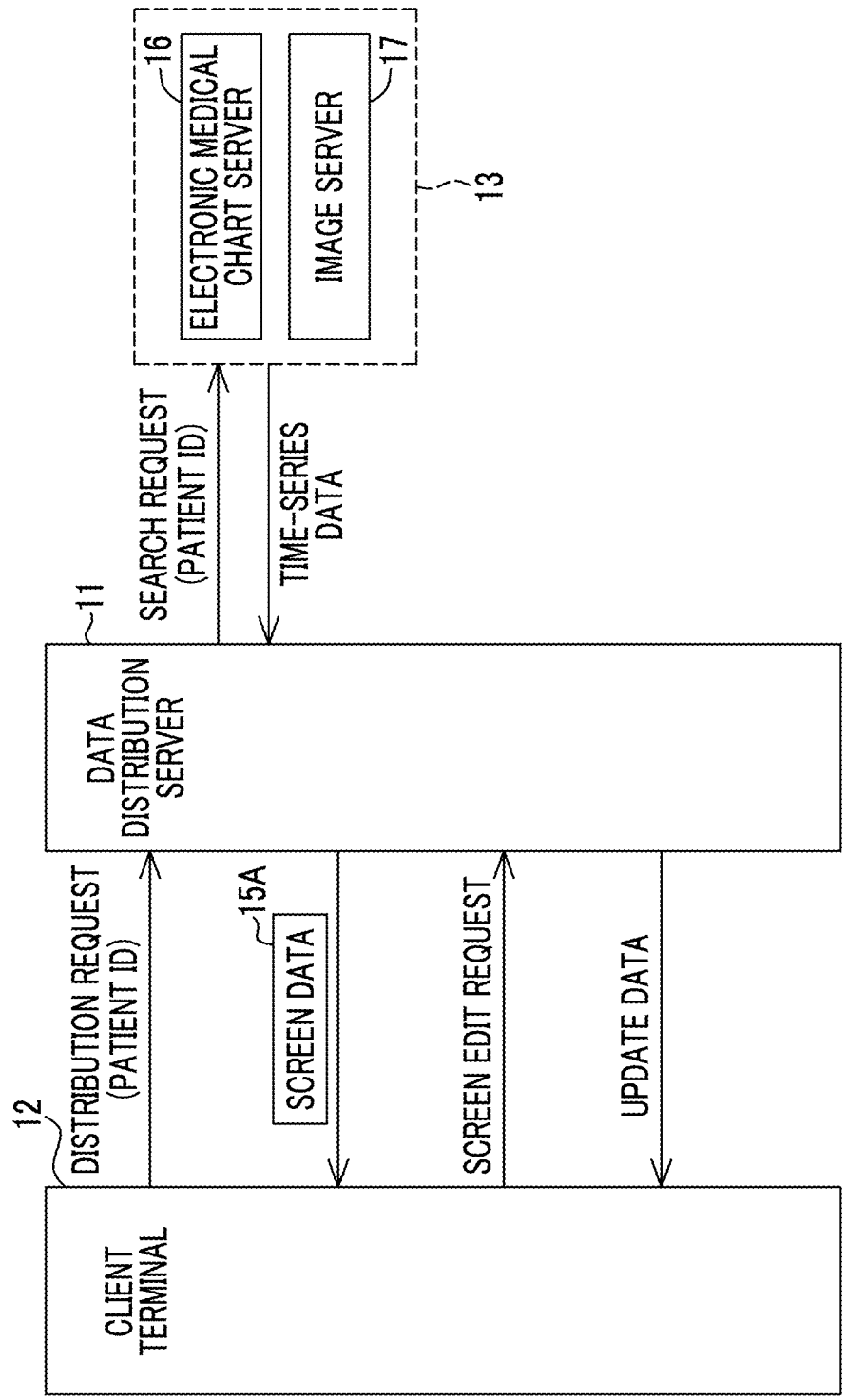
FIG. 4 is an illustrative diagram illustrating a flow of main information of the medical information management system.

As illustrated in FIG. 4, the client terminal 12 receives the patient ID designated by an operation of a doctor, issues a distribution request including the designated patient ID, and transmits the distribution request to the data distribution server 11. Assuming that the data distribution server 11 receives the distribution request from the client terminal 12, the data distribution server 11 transmits a search request for time-series data TS to the electronic medical chart server 16 or the image server 17 using the patient ID as a search key. The electronic medical chart server 16 and the image server 17 search for each item of the time-series data TS regarding the patient ID from the chart DB 16A and the image DB 17A, and transmits the time-series data TS to the data distribution server 11. The data distribution server 11 generates the screen data 15A of the data display screen 15 on the basis of each item of the acquired time-series data TS, and distributes the screen data 15A to the client terminal 12 that is a request source for the distribution request.

The doctor views the data display screen 15 that is displayed on the client terminal 12. In the data display screen 15, screen editing such as changing a screen layout or changing a display item to be displayed in the data display screen 15, such as the time-series data TS to be displayed, can be performed through an editing operation of the doctor. Assuming that the client terminal 12 receives the editing operation, the client terminal 12 issues a screen edit request according to the editing operation and transmits the screen edit request to the data distribution server 11. Assuming that the data distribution server 11 receives the screen edit request, the data distribution server 11 performs an editing process according to content of the screen edit request to generate update data, and distributes the update data to the request source. The client terminal 12 updates the data display screen 15 on the basis of the update data.

The data distribution server 11, the client terminal 12, the electronic medical chart server 16, and the image server 17 are configured by installing a control program such as an operating system or an application program such as a client program or a server program in a computer such as a personal computer, a server computer, or a workstation.

Figure 5:
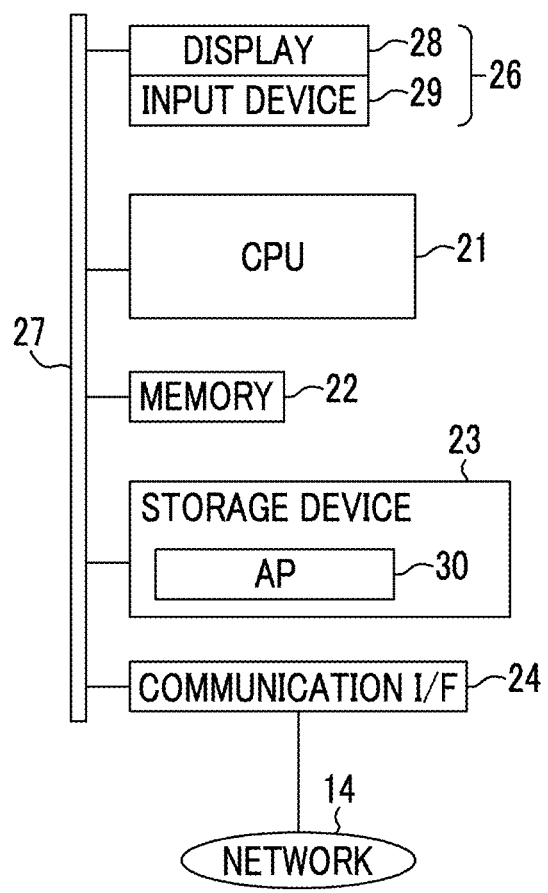

As illustrated in FIG. 5, a computer constituting each server 11, 16, or 17 or the client terminal 12 has the same basic configuration, and includes a central processing unit (CPU) 21, a memory 22, a storage device 23, a communication I/F 24, and an input and output unit 26. These are connected via a data bus 27. The input and output unit 26 includes a display (display unit) 28, and an input device 29 such as a keyboard or a mouse.

The storage device 23 is, for example, a hard disk drive (HDD), and a control program or an application program (hereinafter referred to as an AP) 30 is stored. Further, for example, a disk array in which a plurality of HDDs are connected and mounted is provided as a storage device 23 for a DB separately from the HDD that stores the program, in a server in which a DE is constructed. The disk array may be built into a main body of the server or may be provided separately from the main body of the server and connected to the main body of the server via a cable or a network.

The memory 22 is a work memory used for the CPU 21 to execute a process, and includes a random access memory (PAM). The CPU 21 loads a control program stored in the storage device 23 into the memory 22 and executes a process according to the program to control each unit of the computer. The communication I/F 24 is a network interface that performs transfer control with the network 14.

In the client terminal 12, a client program such as electronic medical chart software for performing viewing or editing of an electronic medical chart, or viewer software for performing viewing of inspection images or the data display screen 15 is installed as the AP 30. The viewer software may be, for example, dedicated software or may be a general-purpose WEB browser.

Figure 6:
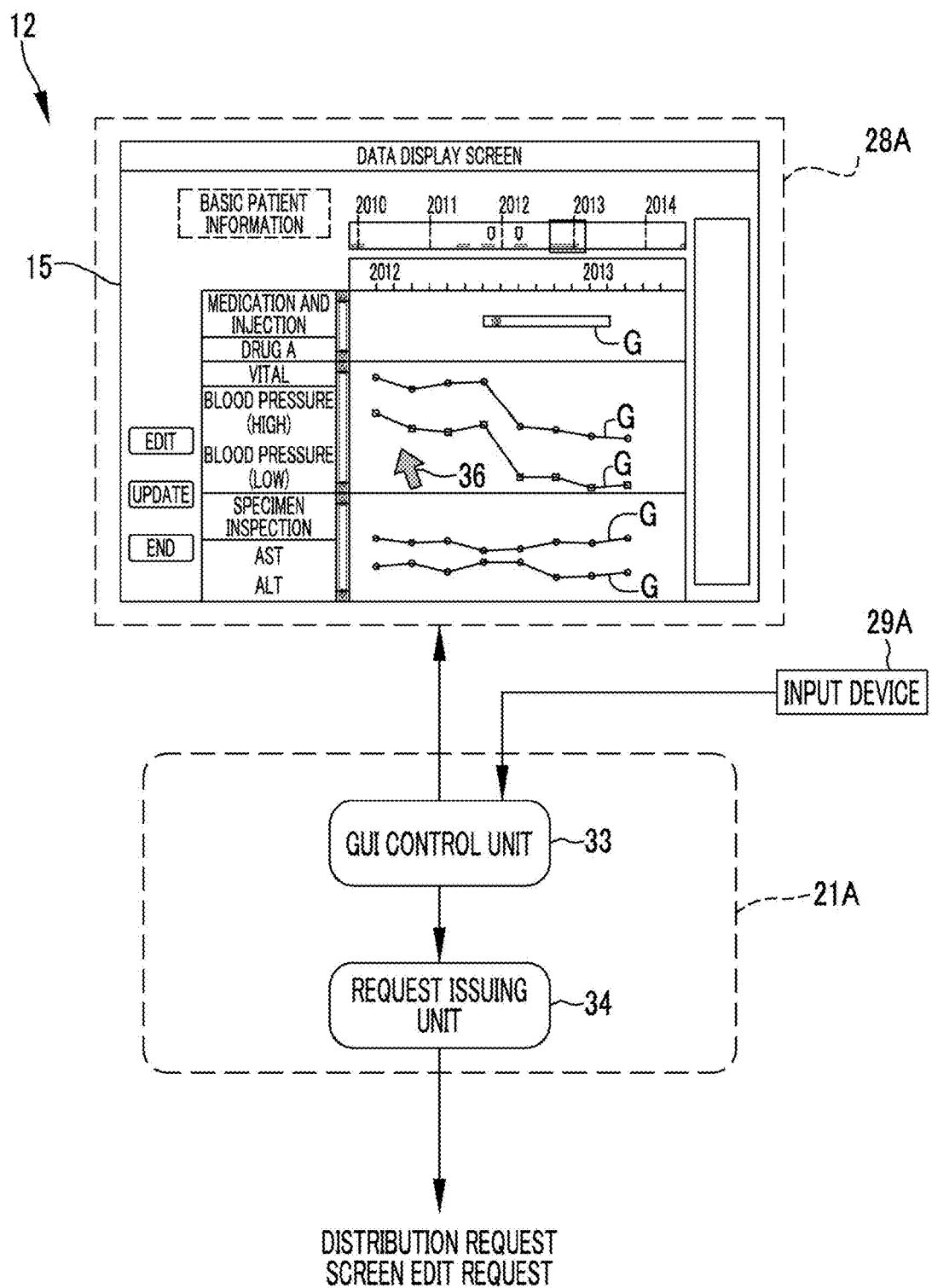
FIG. 6 is an illustrative diagram illustrating a functional overview of a client terminal.

As illustrated in FIG. 6, assuming that the viewer software for displaying the data display screen 15 starts up in the client terminal 12, a start-up screen having an operation function using a graphical user interface (GUI) is displayed on the display 28A of the client terminal 12. The CPU 21A of the client terminal 12 functions as a request issuing unit 34 that issues various requests for the GUI control unit 33 and the data distribution server 11 in cooperation with the memory 22. A designation of the patient ID in the start-up screen or an operation of issuing a distribution request for the screen data 15A of the data display screen 15 is performed.

The screen data 15A includes, for example, data described in a markup language such as Extensible Markup Language (XML), and the data display screen 15 that is reproduced by the screen data 15A also has an operation function using a GUI. The GUI control unit 33 reproduces the data display screen 15 on the basis of the screen data 15A and displays the data display screen 15 on the display 28A. Further, the GUI control unit 33 receives an operation instruction from the input device 29A through the data display screen 15 such as a click operation of an operation button using a pointer 36 of a mouse, and performs a screen control according to the received operation instruction. An instruction to issue the distribution request or the screen edit request is input to the request issuing unit 34 via the GUI control unit 33. The request issuing unit 34 issues a request to distribute the data display screen 15 of the designated patient ID and a screen edit request for the designated content according to the issuing instruction.

Figure 7:
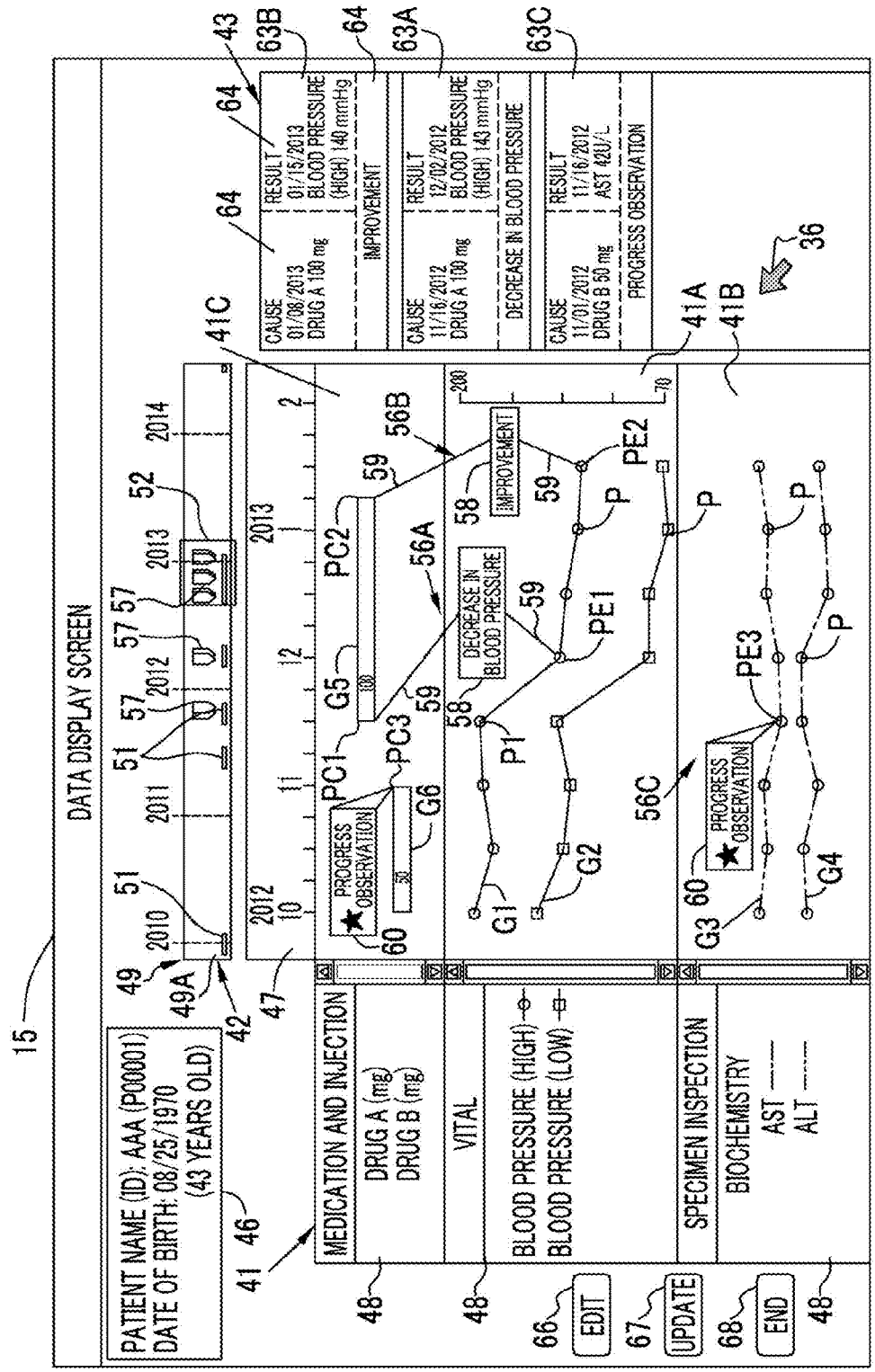
FIG. 7 is an illustrative diagram illustrating an example of a data display screen.

As illustrated in FIG. 7, the data display screen 15 includes a first display area 41, a second display area 42, a list display area 43, and a basic information display area 46. Basic patient information, such as a patient name, patient ID, and age is displayed in the basic information display area 46.

The first display area 41 is a first display area for displaying the time-series data TS (graph G). In the first display area 41, a time is assigned to a horizontal axis. The first display area 41 is divided into a plurality of sub-areas 41A to 41C in a vertical direction. A first time axis 47 of the first display area 41 is provided in an upper portion of the first display area 41. In the first time axis 47, information such as year, month and day, and a scale are arranged according to a set time scale. The first time axis 47 has a length corresponding to the first display period of the first display area 41, and also has a width in a vertical direction so that information can be displayed therein. In this example, the first display period is set to about four months from October 2012 to early February 2013. In the first time axis 47, a numeral indicating the year and the month of the four months corresponding to the first display period, and a scale at a predetermined interval between the months are displayed.

In the first display area 41, data in a range corresponding to the first display period in the time-series data TS is displayed in the form of a graph G (G1 to G6). The first display period can be changed by a screen scroll operation in the horizontal direction. By this screen scroll operation, a display of the year and the month of the first time axis 47 is changed, and a display range of the time-series data TS is changed. In the screen data 15A sent in one distribution from the data distribution server 11, time-series data TS of a longer period than the first display period is included. Therefore, the changing of the display range of the time-series data TS can be performed without redistribution from the data distribution server 11 so long as the range is a received range. In a case in which a change exceeding the received range is performed on the display range of the time-series data TS, additional distribution of the time-series data TS is received from the data distribution server 11.

A plurality of items of time-series data TS acquired in the same period corresponding to the first display period are displayed in the respective sub-areas 41A to 41C. Accordingly, a plurality of items of time-series data TS of the same period of time is comparably displayed. Six time-series data TS of different types are displayed in the form of graphs G1 to G6 in the respective sub-areas 41A to 41O. The type of time-series data TS to be displayed in the respective sub-areas 41A to 41C can be changed by a setting. A type and a name of the time-series data TS, and an item display field 48 for displaying medical care items regarding the time-series data TS are provided in each of the sub-areas 41A to 41O to the left of the respective sub-areas 41A to 41O.

In this example, the sub-area 41A of the second stage from the top is set as an area for displaying the time-series data TS corresponding to vital signs such as blood pressure, body temperature, respiration, and a heart rate. More specifically, as the time-series data TS of the vital signs, the graphs G1 and G2 indicating a transition of measured values of the blood pressure are displayed. The graph G1 is a graph of blood pressure (high), and the graph G2 is a graph of blood pressure (low). The graphs G1 and G2 are line graphs that connect the input points P of a plurality of measured values (individual data) acquired in time series. Further, a scale of the measured value extending in a vertical direction (a lower limit "70" and an upper limit "200" in this example) is provided in a right end in the sub-area 48A. In the item display field 48 corresponding to the sub-area 48A, "vital" is displayed as a name of a large classification of the medical care item, and a name of a measured value indicated by the graphs G1 and G2 of "blood pressure (high)" and "blood pressure (low)" is displayed.

Further, since a plurality of graphs G1 and G2 are displayed within one area in the sub-area 41A, for example, different types of lines on which shapes of the input points P are distinguished by a square or a circle are assigned to the respective graphs G1 and G2 so as to identify the graphs G1 and G2. Line type information indicating the line type of the graphs G1 and G2 corresponding to high or low blood pressure is also displayed in the item display field 48. Although only the blood pressure is displayed as a vital sign in this example, body temperature, heart rate, or the like may be displayed in the sub-area 41A, in addition to the blood pressure. In this case, it is preferable for the line types and colors of the graphs to be changed so that each graph can be identified. It should be understood that only one graph G may be displayed in one sub-area instead of the plurality of graphs G being displayed in one sub-area.

The third stage of sub-area 41B is set as an area for displaying time-series data TS of an inspection value of specimen inspection, and graphs G3 and G4 indicating a transition of the inspection value are displayed. The graphs G3 and G4 are, for example, inspection values of biochemistry inspection, which is one of specimen inspections, the graph G3 is an inspection value of AST (aspartate aminotransferase), and the graph G4 is an inspection value of ALT (alanine aminotransferase). The graphs G3 and G4 are line graphs that connect the input points P of a plurality of inspection values (individual data) acquired in times series, similar to the graphs G1 and G2. "Specimen inspection" as a name of a large classification of the medical care item, "biochemistry" as a name of a middle classification of the medical care item, and "AST" and "ALT" as a name of the inspection value indicated by the graphs G3 and G4 are displayed in the item display field 48 corresponding to the sub-area 41B. Further, line type information for identifying the graphs G3 and G4 are also displayed.

The first stage of the sub-area 41C is set as an area for displaying the time-series data TS of drug administration, such as medication or injection, and graphs G5 and G6 indicating a period in which drug administration has been performed are displayed. Graph G5 is a graph of drug A, and graph G6 is a graph of drug B. In this example, since the dosage of both of drug A and drug B is constant over an entire period, the graphs G5 and G6 are displayed in the form of a bar graph extending straight in a horizontal direction. Assuming that the dosage is changed, the graphs G5 and G6 are changed in the vertical direction. A display indicating numerical values ("100" and "50") of the dosage is inserted into the graphs G5 and G6. "Medication and injection" as a name of a large classification of the medical care item, "Drug A" and "Drug B" as a drug name, "mg" as a unit of the dosage, and the like are displayed in an item display field 48 corresponding to the sub-area 41O.

Further, although not illustrated, a plurality of thumbnail images are arranged along the time axis in a case in which the time-series data TS of the image inspection is displayed in the sub-area. Although the example in which the first display area 41 is divided into three sub-areas has been described in this example, the number of divisions is not limited to three, but may be two or may be three or greater. In a case in which there are the number of sub-areas equal to or greater than the number of sub-areas that can be simultaneously displayed in the first display area 41, a hidden sub-area may be able to be displayed by, for example, the screen scroll operation in the vertical direction. Further, it should be understood that the first display area 41 may not be divided.

The second display area 42 has a relatively longer time scale than the first display area 41, and a second time axis 49 of which the time scale is longer than the first time axis 47 is displayed in the second display area 42. The second time axis 49 has a display frame 49A having a width in a vertical direction in which information can be displayed therein, similar to the first time axis 47. In the second time axis 49, a numeral such as year, month, and day is displayed in an upper portion of the display frame 49A. A scale is displayed in each year inside the display frame 49A. The numeral of year, month and day, and the scale are arranged according to a set time scale.

A length of the second time axis 49 corresponds to the second display period of the second display area 42. The second display period has a longer time scale than the first display period of the first display area 41, and the first display area 41 and the second display area 42 in the data display screen 15 have substantially the same widths. Therefore, for a period of a part in the second time axis 49, detailed display can be performed in the first display area 41.

In FIG. 7, time-series data TS (graph G) corresponding to a part of the second display period is displayed in the first display area 41. In this example, the first display period is set to about four months from October 2012 to early February 2013, and the second display period is set to about four and a half years from 2010 to a first half of 2014 including the first display period of four months. The first display period and the second display period can be changed by a setting.

A data presence indicator 51 indicating that there is the time-series data TS in the second display period is displayed within the display frame 49A of the second time axis 49. Since the presence of the time-series data TS indicates that any medical care has been performed, the data presence indicator 51 also functions as an indicator indicating a day or a period in which the medical care has been performed. The data presence indicator 51 is, for example, a bar-shaped indicator extending in the direction of the second time axis 49. Further, a period indicator 52 is displayed in the display frame 49A.

The period indicator 52 is an indicator indicating a period to which the first display period of the first display area 41 corresponds on the second time axis 49. A width of the period indicator 52 corresponds to a length of the first display period in the time scale of the second time axis 49. In this example, since the first display period is about four months, the width of the period indicator 52 corresponds to a width of about four months in the time scale of the second time axis 49. Further, the period indicator 52 also functions as an operation portion for changing the first display period of the first display area 41. The period indicator 52 includes an operation portion slidable on the second time axis 49. Assuming that the period indicator 52 is designated by the pointer 36 and a slide operation is performed, the first display period of the first display area 41 is also changed. For example, assuming that the period indicator 52 is moved from a position of 2013 to a position of 2012 in the second time axis 49 by the slide operation, the first display period displayed in the first display area 41 is changed from 2013 to 2012.

Since the data presence indicator 51 is displayed in the second time axis 49, the time-series data TS of a movement destination can be displayed in the first display area 41 assuming that the period indicator 52 is moved to a position of the data presence indicator 51.

Further, in the data display screen 15, an association indicator 56 indicating that at least two designated positions including the first and second designated positions designated in a plurality of items of time-series data TS are associated with each other can be assigned in the first display area 41. The time-series data TS in which the first designated position is designated is first time-series data, and the time-series data TS in which the second designated position is designated is second time-series data. In a case in which the association indicator 56 is assigned, it is necessary for at least one point to be designated as a designated position in each of a plurality of items of time-series data TS. In the case of the graphs G1 to G4, at least any one of a plurality of input points P of individual data may be designated as the designated position. In the case of the graphs G5 and G6, at least any one of points on the graphs G5 and G6 may be designated.

Further, in the case of the graphs G5 and G6 of medication, continuous medication is performed in a predetermined period. As described above, in the medication, the medication in a predetermined period may be instructed in one prescription, and individual data may be recorded in units of prescriptions. In a case in which the graph G5 or the graph G6 is an individual data group for one prescription, each of items of the time-series data TS of the graph G5 or the graph G6 includes a plurality of pieces of individual data, but substantially corresponds to one item of the individual data. In such a case, although the designated position in the time-series data TS in the graph G5 or the graph G6 is for the individual data, but an entire predetermined period can be interpreted as the designated position and set at a designated point in time. That is, in the case of the medication, even in the event that the individual data is designated by a mouse, a predetermined period corresponding to the individual data is selected, and an association indicator 56A or a tag 58 is input therefor.

Further, although in the case of the medication, a gradual decrease in the amount of the prescription is considered, the individual data group can be recognized based on an increase or a decrease in the amount of prescription. For example, in a case in which a prescription for s gradual decrease in the number of tablets of the drug over six days like six tablets for first two days, four tablets for the next two days, and two tablets next two days in one prescription is performed, a selected predetermined period is two days including day 3 and day 4 assuming that the designated individual data is individual data of day 3. That is, individual data group in which the amount of medication is the same may be treated as a set.

The association indicator 56 is assigned at a position determined to be important by the doctor in the time-series data TS. For example, it can be seen from the graph G1 of blood pressure (high) that a blood pressure transitions to a relatively high state before an input point P1, suddenly decreases between input points P1 and PE1, and is stabilized at a relatively low state after PE1. Meanwhile, it can be seen from the graph G5 of medication (drug A) that medication of drug A starts at the same time as the input point P1 at which the blood pressure starts to decrease. In such a case, a causal relationship between the medication start and the decrease in blood pressure, such as an effect of the decrease in blood pressure due to a cause of the medication, can be confirmed. In a case in which the doctor has made such a determination, the medication start position of the graph G5 is designated as the cause position PC1 corresponding to the cause, the position at which the decrease in blood pressure occurs in the graph G1 is designated as the result the position PE1 corresponding to the result, and the association indicator 56A indicating that the two designated positions are associated with each other is assigned.

The association indicator 56A is a link form in which the association indicator 56A includes a tag 58 and a connection line 59 connecting two designated positions. In this display mode, a first indicator includes one of the connection lines 59 and the tag 58, and a second indicator includes the other of the connection lines 59 and the tag 58. The tag 58 includes an object in which a comment can be displayed and input. A comment "decrease in blood pressure" is input to the tag 58 of the association indicator 56A and displayed.

In a association indicator 56B, an end period of the medication period of the graph G5 of medication (drug A) is designated as a cause position PC2, and a position at which it is observed that the blood pressure is stabilized as a small value and improvement is confirmed in the graph G1 of blood pressure (high) is designated as a result position PE2. The association indicator 56B is in a link form similar to the association indicator 56A, each position is connected by a connection line 59, and "improvement" which is a finding of the doctor is input to the tag 58 of the association indicator 56B and displayed.

In a association indicator 56C, an end period of the medication period of the graph G6 of medication (drug B) is designated as a cause position PC3, and one point of the graph G3 of "AST" is designated as a result position PE3. The association indicator 560 is a pair form including a pair of tags 60 respectively assigned to two designated positions. The pair of tags 60 have the same balloon shape, and the same asterisks are displayed in the two tags 60. Thus, the same shapes or marks of the pair of tags 60 indicate the respective tags 60 are paired and associated. The association indicator 56C in the pair form has a merit of easy drawing unlike the association indicators 56A and 56B in a link form having a thin object such as the connection line 59. Further, there is a merit in that the connection line 59 is not displayed to be overlapped with other graphs, and viewing of graphs or the like is not inhibited.

A comment "progress observation" is input to each of a pair of tags 60 constituting the association indicator 56C and displayed. The tags 60 correspond to the first indicator and the second indicator. Thus, assuming that a causal relationship can be once presumed even in a case in which a definitive judgment cannot be performed for the causal relationship, assignment of the association indicator 56C with the comment "progress observation" facilitates confirmation at the time of subsequent look-back.

Thus, using the association indicator 56, it is possible to simply recognize the causal relationships between two positions in a plurality of items of time-series data TS. In medical care, the association indicator 56 is very useful to recognize the causal relationship on the basis of a plurality of items of data such as the measured values or the inspection values and determine the next medical care plan.

Assuming that the association indicator 56 is assigned, a corresponding indicator 57 is assigned at a corresponding position that temporally corresponds to the association indicator 56 in the second display area 42. The corresponding indicator 57 is an indicator indicating a position in the second time axis at which there is the association indicator 56. The corresponding indicator 57 is assigned at positions corresponding to two designated positions of the association indicator 56, and is displayed within the display frame 49A together with the data presence indicator 51.

In the second time axis 49, the corresponding indicator 57 is not only displayed in a period corresponding to the first display period in which there is the period indicator 52, but also displayed at a position outside the first display period. In this example, the first display period is a period from October 2012 to early February 2013 and there is the period indicator 52 at the position corresponding to that period, but in the second time axis 49, the corresponding indicator 57 is also displayed at a position corresponding to the outside of the first display period such as 2011 or a first half of 2012. Therefore, it is possible to confirm an approximate period of time in which there is the association indicator 56 in the first display period displayed in the first display area 41, as well as in the outside of the first display period.

Further, in the data display screen 15, assuming that any one of the corresponding indicators 57 in the second display area 42 is selected, the first display period of the first display area 41 is changed to a display period including the association indicator 56 corresponding to the selected corresponding indicator 57. As described above, the first display period of the first display area 41 can also be changed by an operation of the period indicator 52 or can be changed by a selection operation of the corresponding indicator 57.

Figure 8:
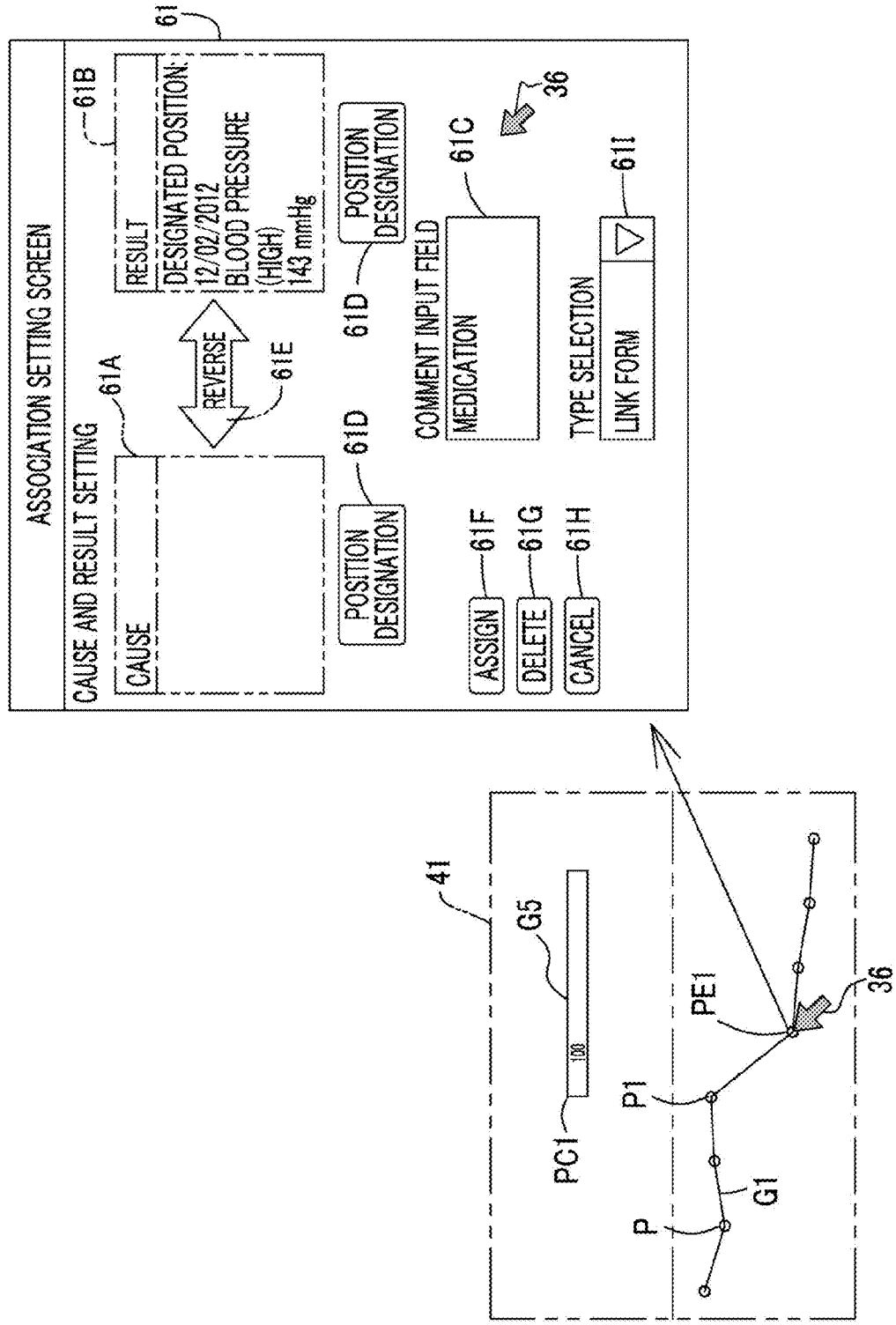
FIG. 8 is an illustrative diagram illustrating an operation of assigning an association indicator.

An assignment operation of the association indicator 56 is performed, for example, in the following procedure. First, an arbitrary position on the graph G is designated by the pointer 36 and a click operation is performed. Assuming that the click operation is performed, an association setting screen 61 illustrated in FIG. 8 is opened on the data display screen 15. In the association setting screen 61, information display fields 61A and 61B in which respective pieces of information on the cause position and the result position are displayed, a comment input filed 61C, a position designation button 61D, a reverse button 61E, an assignment button 61F, a deletion button 61G, a cancel button 61H, and a type selection box 61I are provided.

In the information display field 61A and the information display field 61B, respective pieces of information on individual data corresponding to the cause position and result position are displayed as information on the cause position and the result position. Since the input point P of the graph G1 corresponds to a measured value of the blood pressure (high) in a case in which the input point P on the graph G1 is designated, for example, a name ("blood pressure (high)") of the measured value, measurement date ("2012/12/02"), and a measured value ("143") are displayed in the information display field 61A. In this example, since the result position PE1 is designated, information corresponding to the result position PE1 is displayed.

Figure 9:
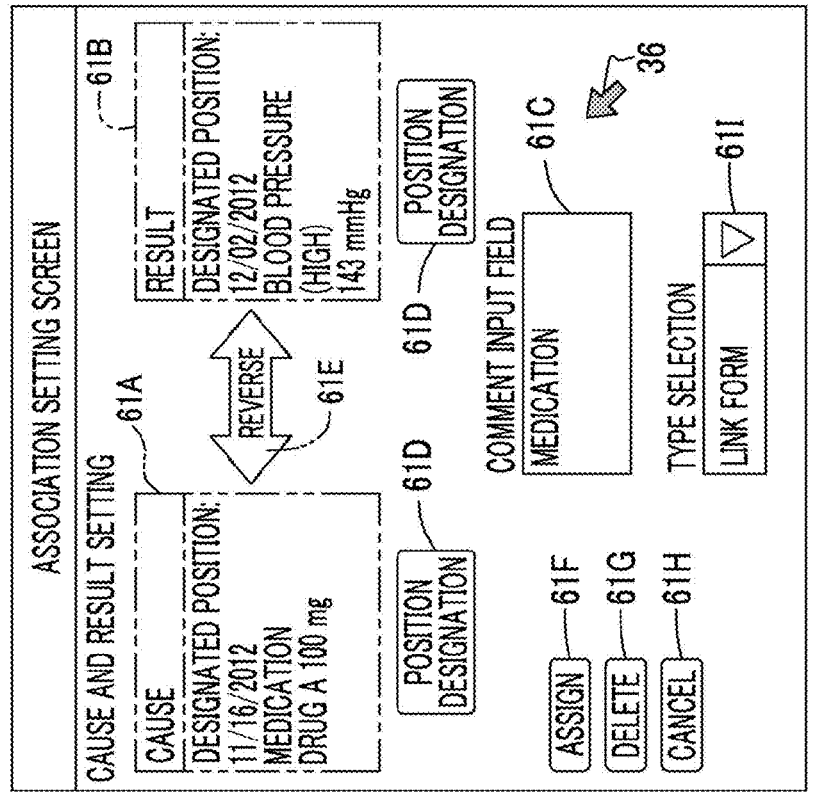
FIG. 9 is an illustrative diagram illustrating an association setting screen in a state in which a cause position and a result position associated with each other have been designated.

In a case in which only one of the cause position and the result position is specified, information is displayed in only one of information display fields 61A and 61B. In this example, for example, information on the result position is displayed in the information display field 61B. Assuming that a position designation button 61D is operated, another designated position can be designated. Assuming that another point on the time-series data TS is designated by the pointer 36, information on another designated position is displayed as illustrated in FIG. 9. In this example, since the cause position PC1 of the graph G5 is designated, information of individual data regarding the medication of the cause position PC1 is displayed.

A reverse button 61E is an operation button for switching between the positions by reversing the cause position and the result position.

A comment input field 61C is an input field for inputting a comment such as "decrease in blood pressure", "improvement", and "progress observation" to the tag 58 or the tag 60. The type selection box 611 is an operation portion for selecting a form of the association indicator 56. In the event that the type selection box 611 is clicked on, for example, a menu for selecting a form of the association indicator 56 such as a link form like the association indicator 56A or a pair form like the association indicator 56C is displayed. Assuming that one type is selected from this menu, the selected type is input to the type selection box 611.

The assignment button 61F is an operation button for inputting an indicator assignment instruction for the association indicator 56. Assuming that the assignment button 61F is operated, the GUI control unit 33 instructs the request issuing unit 34 to issue an indicator assignment instruction of the association indicator 56 of content set in the association setting screen. In this example, the indicator assignment instruction is an association instruction for associating the first designated position with the second designated position.

The deletion button 61G is an operation button for deleting the association indicator 56 that has been once assigned. For example, in the event that the association indicator 56 is designated and clicked on with the pointer 36 even in a case in which the association indicator 56 has been assigned, the association setting screen 61 is opened. In the event that the deletion button 61G is operated at this time, the assigned association indicator 56 is deleted. A cancel button 61H is an operation button for canceling operation content in a state in which the association setting screen 61 is opened. Assuming that the cancel button 61H is operated, return to a state before the association setting screen 61 is opened occurs.

In the event that such an assignment operation of the association indicator 56 is performed, the request issuing unit 34 issues a screen edit request including an indicator assignment instruction of the association indicator 56. The screen edit request is transmitted to the data distribution server 11.

In FIG. 7, the list display area 43 is an area in which content of a plurality of association indicators 56 are displayed as a list. In the list display area 43, a plurality of set information 63A to 63C indicating content of the respective indicators are displayed for a plurality of association indicators 56A to 56C displayed in the first display area 41. The respective set information 63A to 63C are arranged, for example, in a vertical direction in a list format.

The set information 63 is created for each association indicator 56 as described below (see FIG. 11). The content of the set information 63 is information such as information on the cause position and the result position at which the association indicator 56 has been assigned and, specifically, individual data (a measured value, an inspection value, a dosage, or the like) corresponding to the cause position and the result position, date of the individual data, a name ("blood pressure (high)", "AST", or the like) of the individual data, and an input comment. For example, in the set information 63A corresponding to the association indicator 56A, date ("2012/11/16") of the cause position PC1, a drug name ("drug A"), and a dosage ("100") are displayed as the content of the cause position PC1. Date ("2012/12/02") of the result position PE1, a name ("blood pressure (high)") of the individual data, and a measured value ("143") of the individual data are displayed as the content of the result position PE1. Further, content of the comment "decrease in blood pressure" is also displayed.

A display field of each piece of set information 63 is partitioned into three sub-display fields 64, and the content of the cause position, the content of the result position, and the comment input to the tag are displayed in the respective sub-display fields 64. Since the cause position and the result position are distinguished and displayed by the sub-display field 64, it is possible to confirm the content of the cause position and the result position at a glance.

Further, in this example, the set information 63 corresponding to the association indicator 56 displayed in the first display area 41 is displayed in the list display area 43. In a case in which the first display period of the first display area 41 is changed by a screen scroll operation, the displayed association indicator 56 is also changed. Therefore, it is preferable for the set information 63 of the list display area 43 to be changed in conjunction with the change in the association indicator 56 displayed in the first display area 41.

Further, a target range of the set information 63 displayed in the list display area 43 may include the corresponding indicator 57 displayed in the second display area 42, instead of the association indicator 56 displayed in the first display area 41. In a case in which the corresponding indicator 57 is a target, it is possible to confirm, in the list display area 43, content of an association indicator 56 other than the association indicator 56 displayed in the first display area 41.

Further, an order of a display of a plurality of set information can be changed in the list display area 43. In this example, respective pieces of set information 63A to 63C are sorted in an order of date of individual data and displayed in the list display area 43. A sorting condition for changing the display order of the respective pieces of set information 63A to 63C can include, for example, an order of date on which the association indicator 56 is assigned, in addition to date on which the individual data is acquired. The operation instruction of such a sorting process is performed, for example, by a mouse click operation. For example, a pop-up menu in which a plurality of sorting conditions (an order of date of individual data, an order of creation of the set information, or the like) are displayed is displayed by the click operation. A sorting operation instruction is input by selecting one sorting condition in the pop-up menu. It should be understood that the sorting condition can include various sorting conditions or may include an order of access of editing or viewing of the set information 63.

An edit button 66, an update button 67, and an end button 68 are provided to the left of the first display area 41 on the data display screen 15. The edit button 66 is an operation button for performing screen editing of the data display screen 15. Assuming that the edit button 66 is operated, for example, an edit menu screen (not illustrated) for instructing the screen editing pops up. Screen editing items include, for example, a setting of a display period or a time scale of the first display area 41 and the second display area 42, and a setting of the number of divisions of sub-areas of the first display area 41. Further, there is a setting of display items such as the time-series data TS displayed in each sub-area or information displayed in areas other than the item display field 48. A screen layout may be changed. For example, the display positions of the first display area 41 and the second display area 42 are reversed. Further, a menu item for assigning the association indicator 56 may be displayed in the edit menu screen.

Assuming that the screen editing is instructed by the editing menu screen, the request issuing unit 34 issues a screen edit request according to designated content, and the screen edit request is transmitted to the data distribution server 11.

The update button 67 is an operation button for updating the data display screen 15. In a case in which any screen editing instruction is input at the point in time at which the update button 67 is operated, the request issuing unit 34 issues a screen edit request including the input screen editing instruction assuming that the update button 67 is operated. Assuming that there is no screen edit instruction, the request issuing unit 34 issues a distribution request to reload the screen data 15A of the data display screen 15 in an editing state at that point in time. The end button 68 is an operation button for ending the data display screen 15.

Figure 10:
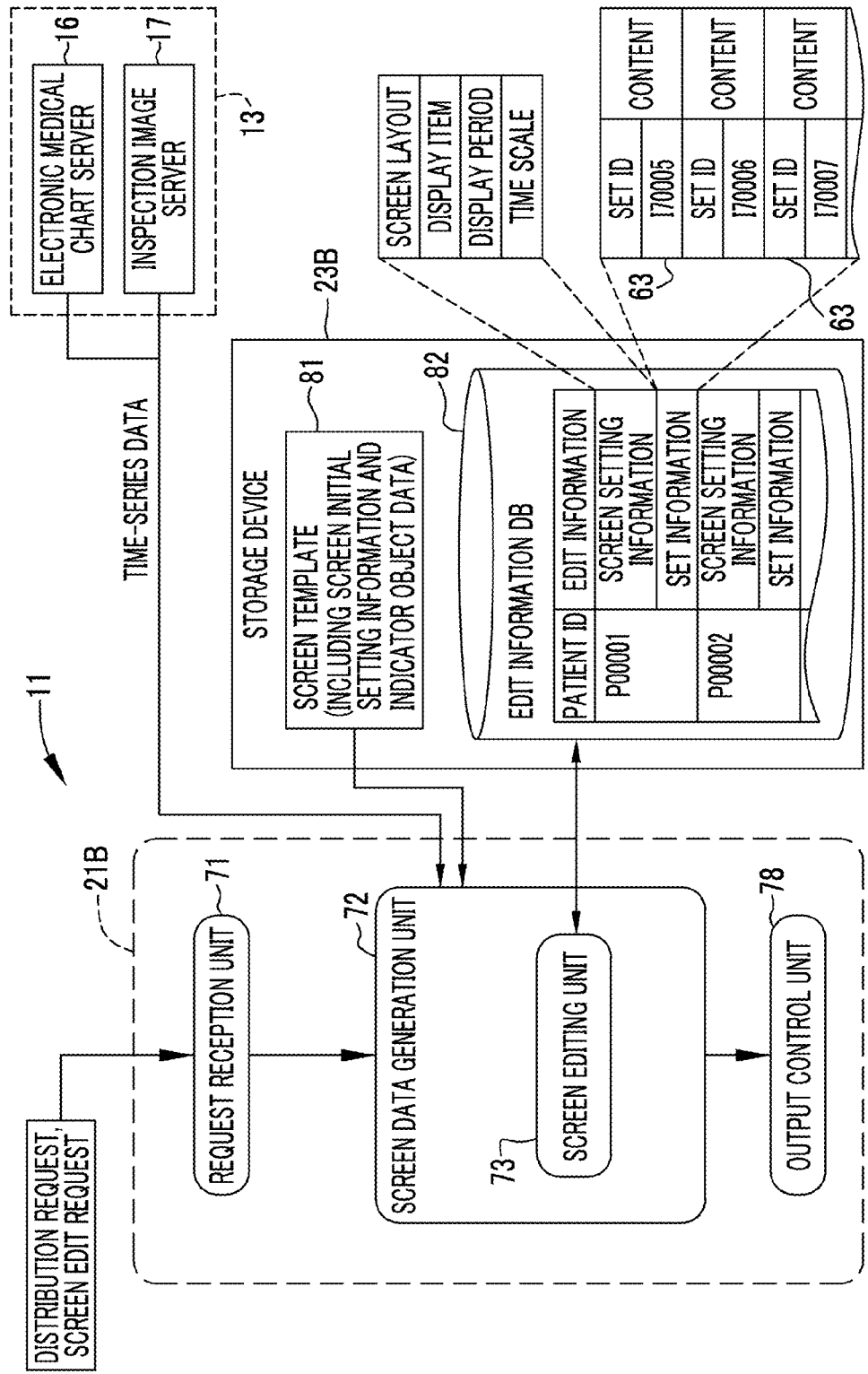
FIG. 10 is an illustrative diagram illustrating a schematic function of a data distribution server.

As illustrated in FIG. 10, a data distribution server program is installed as an AP 30 in the data distribution server 11. Assuming that the program is executed, the CPU 21B of the data distribution server 11 functions as a request reception unit 71, a screen data generation unit 72, and an output control unit 78 in cooperation with the memory 22. The request reception unit 71 receives various requests from the client terminal 12. In a case in which the request reception unit 71 receives a distribution request or a screen edit request, the request reception unit 71 inputs the received request to the screen data generation unit 72. This request reception unit 71 is an association assignment instruction reception unit that receives an indicator assignment instruction as an association instruction included in the screen edit request.

The screen data generation unit 72 generates the screen data 15A of the data display screen 15 for displaying the time-series data TS regarding the patient ID designated in the distribution request on the basis of the input distribution request. The screen data 15A is XML data for WEB distribution, as described above. In the event that the screen data generation unit 72 generates the screen data 15A, the screen data generation unit 72 uses a screen template 81 and an edit information DB 82 stored in the storage device 23B of the data distribution server 11. A screen editing unit 73 is provided in the screen data generation unit 72. The screen editing unit 73 edits the screen data 15A on the basis of the edit information.

The screen template 81 includes data such as an initial screen setting information on the data display screen 15 or indicator object data. The initial screen information is initial setting information, such as a display period or a time scale of each of the first display area 41 and the second display area 42, the number of divisions of the first display area 41, and a screen layout in the data display screen 15. The indicator object data is object data such as icons inserted into the data display screen 15, such as the association indicator 56 or the corresponding indicator 57.

The edit information DB 82 is a database that stores edit information in a case in which a user has edited the data display screen 15. In the data display screen 15, since the time-series data TS is displayed in units of patients, the edit information is also stored for each patient ID. The edit information includes the screen setting information on the screen layout, display items, the display period, and the time scale, and set information 63 on the association indicator 56. One piece of set information is created for one association indicator 56. One piece of set information 63 includes indicator information of the association indicators 56, and a plurality of pieces of individual data corresponding to a plurality of designated positions (cause positions and result positions) of the association indicators 56. In a case in which a plurality of association indicators 56 are assigned, a plurality of pieces of indicator information are stored. An indicator ID is assigned to each piece of indicator information. Causal relationship information indicating that one is a cause and the other is a result is recorded for a plurality of pieces of individual data in the set information 63.

The screen data generation unit 72 reads the edit information of the designated patient ID from the edit information DB 82 on the basis of the distribution request. The screen data generation unit 72 checks the display items such as the time-series data TS displayed on the data display screen 15 on the basis of the screen setting information of the edit information, and acquires the time-series data TS from the server group 13.

In a case in which there is the edit information on the designated patient ID, the screen editing unit 73 processes the screen template 81 to perform a screen editing on the basis of the edit information. For example, the screen editing unit 73 converts the acquired time-series data TS into a graph display form according to the display period or the time scale of the first display area 41 within the edit information. The graph after conversion is inserted into the screen template 81. Further, in a case in which there is, for example, a designation of the screen layout in the edit information, the designated screen editing is performed to generate the screen data 15A. In a case in which there is the set information 63 in the edit information, the set information 63 is also added in the screen data 15A. Further, individual data of a part corresponding to the display range of the time-series data TS and at least a part including a part before and after such a part is added to the screen data 15A. In a case in which the time-series data TS is an image, for example, a thumbnail image is added.

Further, in a case in which the screen edit request is received after the screen data 15A is distributed, the screen editing unit 73 performs screen editing according to the screen edit request and generates update data. The update data, for example, may be the entire updated screen data 15A or may be a part required for update. Further, the screen editing unit 73 updates the edit information in the edit information DB 82 with content of the received screen edit request.

Figure 11:
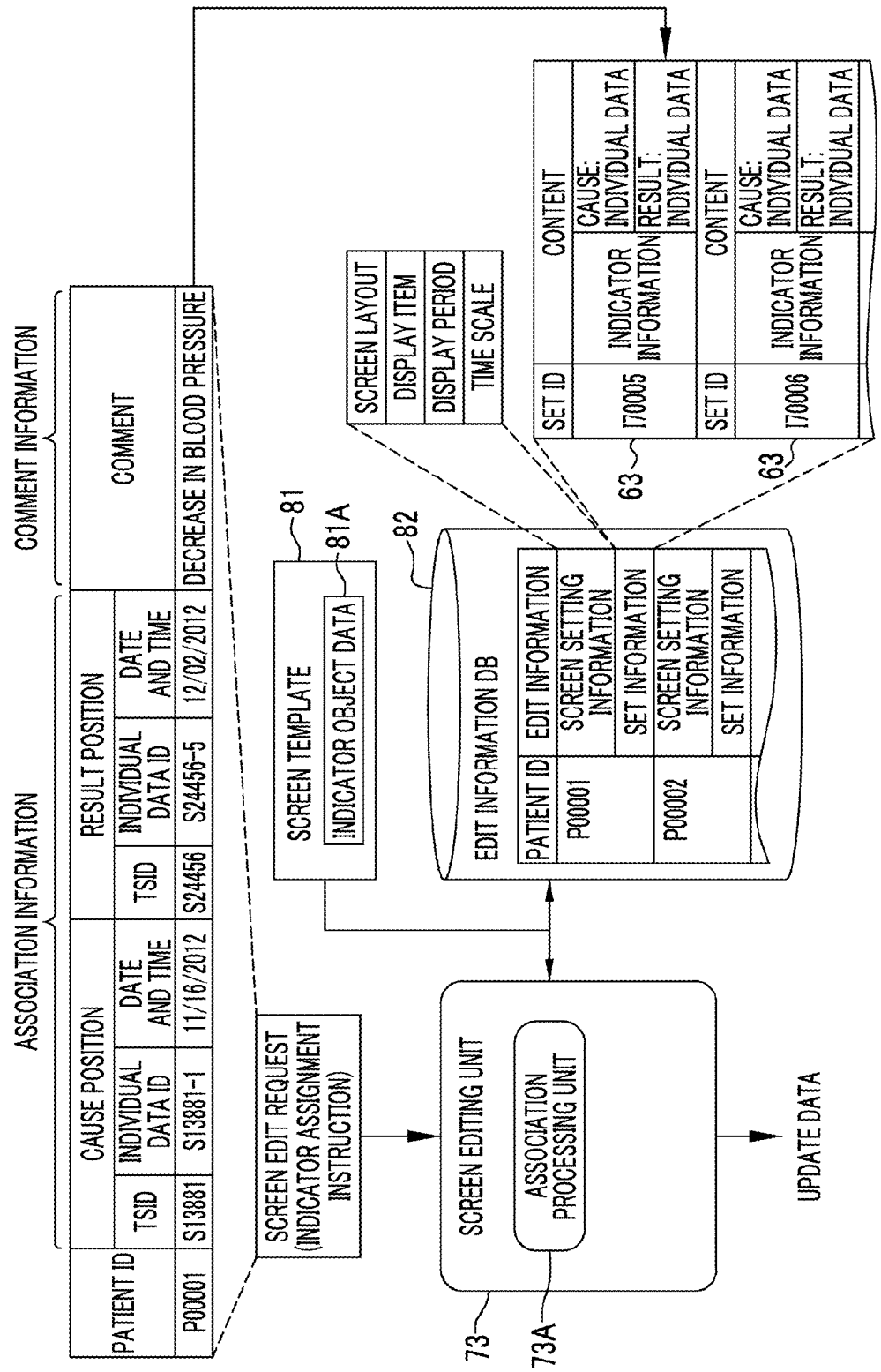
FIG. 11 is an illustrative diagram illustrating a schematic function of a screen editing unit regarding an indicator assignment instruction.

As illustrated in FIG. 11, an association processing unit 73A is provided in the screen editing unit 73. The association processing unit 73A performs an association process of the cause position and the result position by assigning the association indicator 56. In a case in which there is an indicator assignment instruction for the association indicator 56 in a newly received screen editing request or in a case in which the set information has already been stored in the edit information, the association processing unit 73A assigns the association indicator 56 and the corresponding indicator 57 on the basis of the indicator assignment instruction or the set information in one screen editing.

Further, the association processing unit 73A stores content of the received screen editing request including the indicator assignment instruction as edit information within the edit information DB 82. In the case of the indicator assignment instruction, indicator information including the content of the indicator assignment instruction, and the individual data corresponding to the cause position and result position are stored as one piece of set information 63. A set ID is assigned to each piece of set information 63. Further, the association processing unit 73A also records creation date and time in the set information 63 in the event of storing the set information 63. The creation date and time of the set information 63 substantially corresponds to the assignment date and time of the association indicator 56.

Association information including information on the cause position and the result position, and input comment information are included corresponding to the content set in the association setting screen 61, in the indicator assignment instruction, in addition to the patient ID. The association information indicates that the cause position and the result position are associated with each other, and is information for associating the cause position and the result position with each other. The association information includes TSID of the time-series data TS, an individual data ID, and time and date information for each of the cause position and the result position. Further, the indicator information includes the association information and the comment information. The storage device 23B functions as a storage unit that stores the association information included in the indicator information.

The association processing unit 73A reads the designated position from the newly received indicator assignment instruction or the indicator information within the read set information, specifies the cause position and the result position in the time-series data TS (graph G) designated within the data display screen 15, and assigns the association indicator 56 at the specified cause position and the specified result position. The association processing unit 73A specifies the corresponding position within the second display area 42 according to the specified cause position and the specified result position and the time scale of the first display area 41 and the second display area 42, and assigns the corresponding indicator 57 at the specified corresponding position.

In FIG. 10, meanwhile, in a case in which screen data 15A of a new patient ID is generated, the screen data generation unit 72 generates the screen data 15A as an initial setting according to the screen template 81. In this case, the time-series data TS to be displayed may be determined, for example, with initial screen setting information, like a display of "blood pressure" and "body temperature" for the vital, and selection of the time-series data TS may be inquired of the client terminal 12. In this case, the screen data generation unit 72 waits for the selection information for the time-series data TS from the client terminal 12, receives the selection information, acquires the time-series data TS from the server group 13, and then generates the screen data 15A.

The output control unit 78 performs control to distribute the screen data 15A generated by the screen data generation unit 72 or the update data to the client terminal 12 that is a request source. The client terminal 12 displays the data display screen 15 on the display on the basis of the received screen data 15A or the update data.

Further, the GUI control unit 33 of the client terminal 12 performs changing of the display of the set information 63 that is in conjunction with the first display period in the list display area 43, or a sorting process according to a sorting condition regarding each piece of set information 63 in the list display area 43, on the basis of the received screen data 15A. Since the set information 63 is included in the screen data 15A, the GUI control unit 33 processes the display changing or the sorting process on the basis of the set information 63. For the display change, in a case in which the first display period is changed, the GUI control unit 33 specifies the association indicator 56 displayed in the first display area 41, and displays the set information 63 corresponding to the specified association indicator 56 in the list display area 43.

Further, for the sorting, assuming that a sorting operation instruction is input, the GUI control unit 33 sorts the set information 63 according to the sorting condition. For example, in a case in which the sorting condition is an order of date of the individual data, the GUI control unit 33 sorts the set information 63 in the list display area 43 in an order of the date of the individual data corresponding to the set information 63. Further, in a case in which the sorting condition is an order of creation of the set information 63, the GUI control unit 33 sorts the set information 63 on the basis of creation date and time within the set information 63.

Thus, the GUI control unit 33 performs the display changing or the sorting on the basis of the screen data 15A without a request from the client terminal 12 to the data distribution server 11 in a range of the set information 63 included in the received screen data 15A. In a range of the set information 63 not included in the screen data 15A, the GUI control unit 33 requests the data distribution server 11 to provide the update data. It should be understood that the data distribution server 11 may be caused to process the request instead of the client terminal 12 processing the display changing or the sorting.

Figure 12:
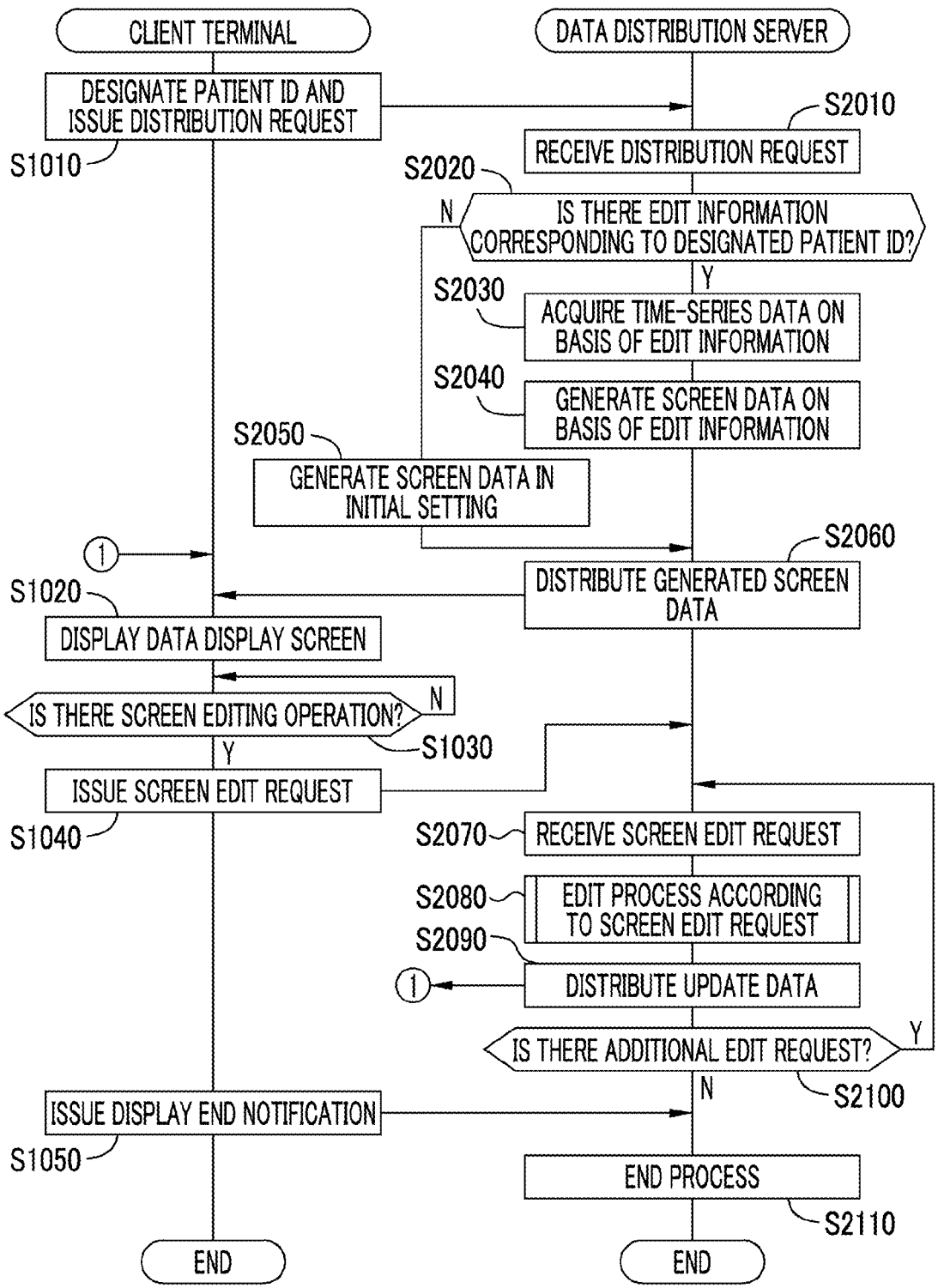
FIG. 12 is a flowchart illustrating a schematic procedure of a display and editing of a data display screen.
Figure 13:
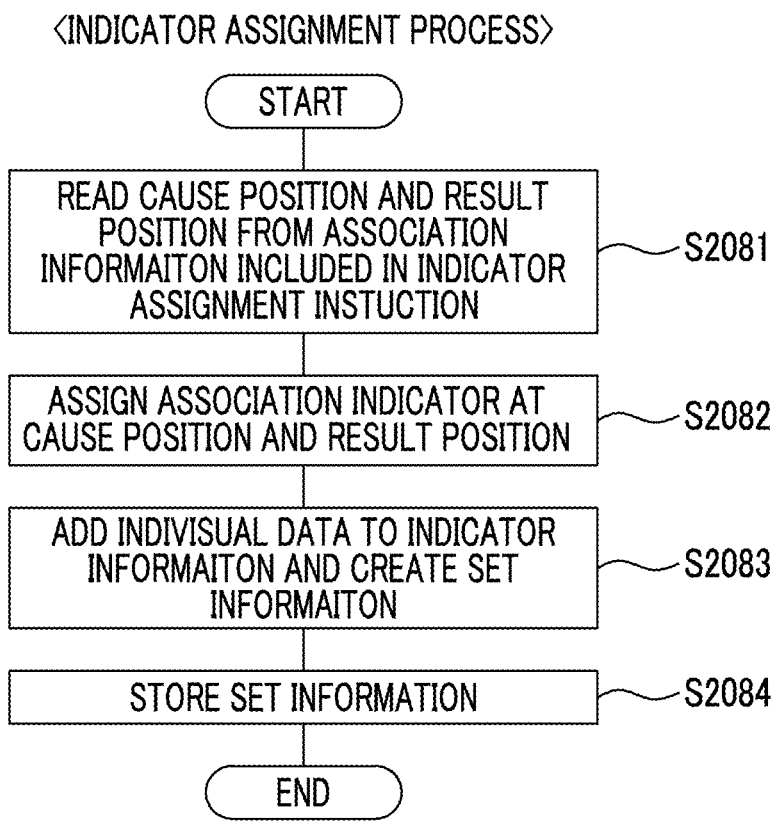
FIG. 13 is a flowchart illustrating a procedure of assigning an association indicator.

Hereinafter, an operation of the above configuration will be described with reference to FIGS. 12 and 13. In the event that the data display screen 15 is displayed, the viewer software starts up in the client terminal 12. A patient ID is designated in the start-up screen by the doctor, and a distribution request is issued (S1010). The distribution request is transmitted from the client terminal 12 to the data distribution server 11. Assuming that the data distribution server 11 receives the distribution request (S2010), the screen data generation unit 72 extracts the patient ID included in the distribution request, and reads edit information of the designated patient ID from the edit information DB. In a case in which there is the edit information corresponding to the designated patient ID (Y in S2020), the time-series data TS designated by screen setting information in the edit information is acquired from the server group 13 (S2030). The screen editing unit 73 generates the screen data 15A on the basis of the acquired time-series data TS and the edit information (S2040). In a case in which there is the set information 63 in the edit information, the screen editing unit 73 performs, for example, a process of assigning the association indicator 56 to the screen data 15A on the basis of the set information 63. On the other hand, in the case of a new patient ID, since there is no edit information (N in S2020), the screen data generation unit 72 generates the screen data 15A in an initial setting.

The data distribution server 11 distributes the generated screen data 15A to the client terminal 12 (S2060). The client terminal 12 reproduces the data display screen 15 on the basis of the received screen data 15A and displays the data display screen 15 on the display (S1020). The client terminal 12 waits for a screen editing operation such as an operation of assigning the association indicator 56 (S1030). In a case in which there is the screen editing operation (Y in S1030), the client terminal 12 issues a screen edit request (S1040).

Assuming that the data distribution server 11 receives the screen edit request (S2070), the screen editing unit 73 performs an editing process according to the screen edit request (S2080). In a case in which there is an indicator assignment instruction in the screen edit request, the screen editing unit 73 reads the cause position and the result position from the indicator assignment instruction (S2081). The screen editing unit 73 assigns the association indicator 56 at the cause position and the result position in the first display area (S2082). The screen editing unit 73 assigns the corresponding indicator 57 at a corresponding position corresponding to the association indicator 56 in the second display area 42. Further, the screen editing unit 73 generates the association information and the comment information of the cause position and the result position read from the indicator assignment instruction as indicator information, and adds the individual data corresponding to the cause position and result position to the indicator information to create the set information 63 (S2083). The screen editing unit 73 generates update data to which the association indicator 56 and the corresponding indicator 57 have been assigned. After assigning the association indicator 56, the screen editing unit 73 stores the set information 63 in the edit information DB 82 as edit information (S2084).

In the case of a screen edit request other than the indicator assignment instruction, the screen editing unit 73 performs screen editing and generation of update data according to designated content, and stores edit information in the edit information DB 82. The data distribution server 11 distributes the generated update data (S2090). The client terminal 12 updates and displays the data display screen 15 on the basis of the update data (S1020).

In the data display screen 15, the association indicator 56 is displayed in the first display area 41. As illustrated in FIG. 7, the association indicator 56 is assigned at a position determined to be important by the doctor. Specifically, the association indicator 56 is assigned in a case in which the causal relationship in a plurality of items of time-series data TS is admitted by the doctor, like the medication start and the decrease in blood pressure. Since the association indicator 56 is assigned with any one point of each of the plurality of items of time-series data TS designated as the cause position and the result position, it is possible to simply recognize the causal relationship of the cause position and the result position. Since at the cause position and the result position, one point in each piece of the time-series data TS can be designated as a pinpoint, it is possible to clearly recognize the causal relationship between an important change point in time, such as the decrease in blood pressure, and a medication start point in time.

Further, even in a case in which an effect of the medication of which a point in time of effect expression is different is monitored for each patient, for example, a point in time at which the dosage has changed and a point in time at which the inspection value has changed can be recorded to be associated by the association indicator 56. Thus, according to the present invention, since the causal relationship between any points in time in the plurality of items of time-series data TS can be simply recognized, it is possible to record useful information in actual medical care, unlike the related art. Therefore, since the causal relationship can be simply recognized even in the event that the data is looked back later, efficiency of the medical care is also improved.

Further, since the plurality of pieces of set information 63 corresponding to the plurality of association indicators 56 are displayed as a list in the list display area 43, it is possible to simply recognize content of the association indicator 56.

Further, in addition to the association indicator 56, a corresponding indicator 57 is displayed at a position corresponding to the association indicator 56 in the second display area 42. Since the second display area 42 has a longer time scale than the first display area 41, it is possible to simply find the association indicator 56 not displayed in the first display area 41 such as the association indicator 56 assigned in the past, by searching for the corresponding indicator 57 in the second display area 42. Therefore, it is possible to recognize the entire image regarding the important point in time regarding the medical care by confirming the position of the corresponding indicator 57 in the second display area 42 and to simply recognize a detailed change in the time-series data at the important point in time at which the association indicator 56 has been assigned by confirming the association indicator 56 in the first display area 41.

In the case of a patient visiting a hospital or hospitalized over a relatively long period, an acquisition period of the time-series data is also a long period. Since the first display area 41 is an area for confirming a fine change in the time-series data, the time scale is short and a display range of the time-series data is narrow. Therefore, since a proportion that can be displayed in the first display area 41 decreases as an acquisition period of the time-series data increases, the number of association indicators 56 that are not displayed in the first display area 41 increases, and a risk of oversight of the previous important first association indicators 56 increases in the event that the time-series data is looked back. According to this example, since the corresponding indicator 57 indicating the presence of the association indicator 56 is displayed in the second display area 42 having a longer time scale, it is possible to reduce a risk of oversight of the important association indicator 56 even in the event that the acquisition period of the time-series data is long.

The data distribution server 11 waits for an additional screen edit request after the distribution of the update data (S2100). Assuming that there is the additional screen edit request, the above procedure is repeated.

In the client terminal 12, assuming that the end button 68 of the data display screen 15 is operated, the data display screen 15 ends. The client terminal 12 issues a display end notification (S1050). Assuming that the data distribution server 11 receives the display end notification, the data distribution server 11 performs a termination process. In a case in which the distribution request is received again, the process from S2010 is repeated. The end process is executed in a case in which there is no request from the client terminal 12 for a defined time (so-called timeout), in addition to a case in which the end notification is received.

In this example, since the association indicator 56 is in the form of a tag in which a comment can be input and displayed, a judgment or thought process of the doctor in the event that the association indicator 56 is assigned, such as a reason for assignment of the association indicator 56 and a meaning of data at the designated position at which the association indicator 56 is assigned, can be input as a memo of a memorandum book. Accordingly, it is convenient at the time of subsequent look-back. The association indicator 56 is not limited to the form of the tag and the comment may be unable to be input. Further, a comment may also be displayed in the corresponding indicator 57.

Further, in this embodiment, the indicator information on the association indicator 56 is not directly added to the time-series data TS, but are included in the edit information created separately from the time-series data TS and stored separately from the server group 13 in which the time-series data TS is stored. In a case in which the indicator information is directly added to time-series data TS, the server group 13 that stores time-series data TS may be required to be remodeled, but in this example, such remodeling is not necessary. It should be understood that, in a case in which the time-series data TS to which the indicator information is added can be stored in the server group 13 or remodeling is allowed, the indicator information may be directly added to the time-series data TS.

Further, in this embodiment, since the data distribution server 11 acquires the time-series data TS from the server group 13 for each distribution request instead of storing the acquired time-series data TS, a storage space for time-series data TS in the data distribution server 11 can be reduced. Further, even in the event that the time-series data TS is stored in the data distribution server 11, it is necessary for at least a difference data to be acquired from the server group 13 for each distribution request in order to update to the recent time-series data TS. Therefore, since there is no great difference in a processing time including a data acquisition time even in the event that the acquired time-series data TS is stored, it is advantageous not to store the time-series data TS as in this example since the storage space can be reduced.

Although a link form of the association indicator 56A illustrated in FIG. 7 and a pair form of the association indicator 56C are illustrated as a form of the association indicator 56 in this example, the form may be another form. For example, in a modification example of the pair form, only one of a pair of tags 60 is displayed and the other is hidden in an initial state, and assuming that the displayed tag 60 is selected by the pointer 36, the hidden tag 60 may also be displayed. Since a situation in which the association indicators 56 are rather not well seen occurs in the event that the number of the association indicators 56 increases, a form in which tags to be displayed are minimized is effective from such a point of view.

Further, the association indicators 56 are designated at positions determined to be important by the doctor, but degrees of importance may be relatively different among a plurality of association indicators 56. Therefore, the association indicator 56 having a high degree of importance may be displayed to be distinguishable by changing a form of an icon, color, or the number of asterisks of the association indicator 56 according to the degree of importance.

Figure 14:
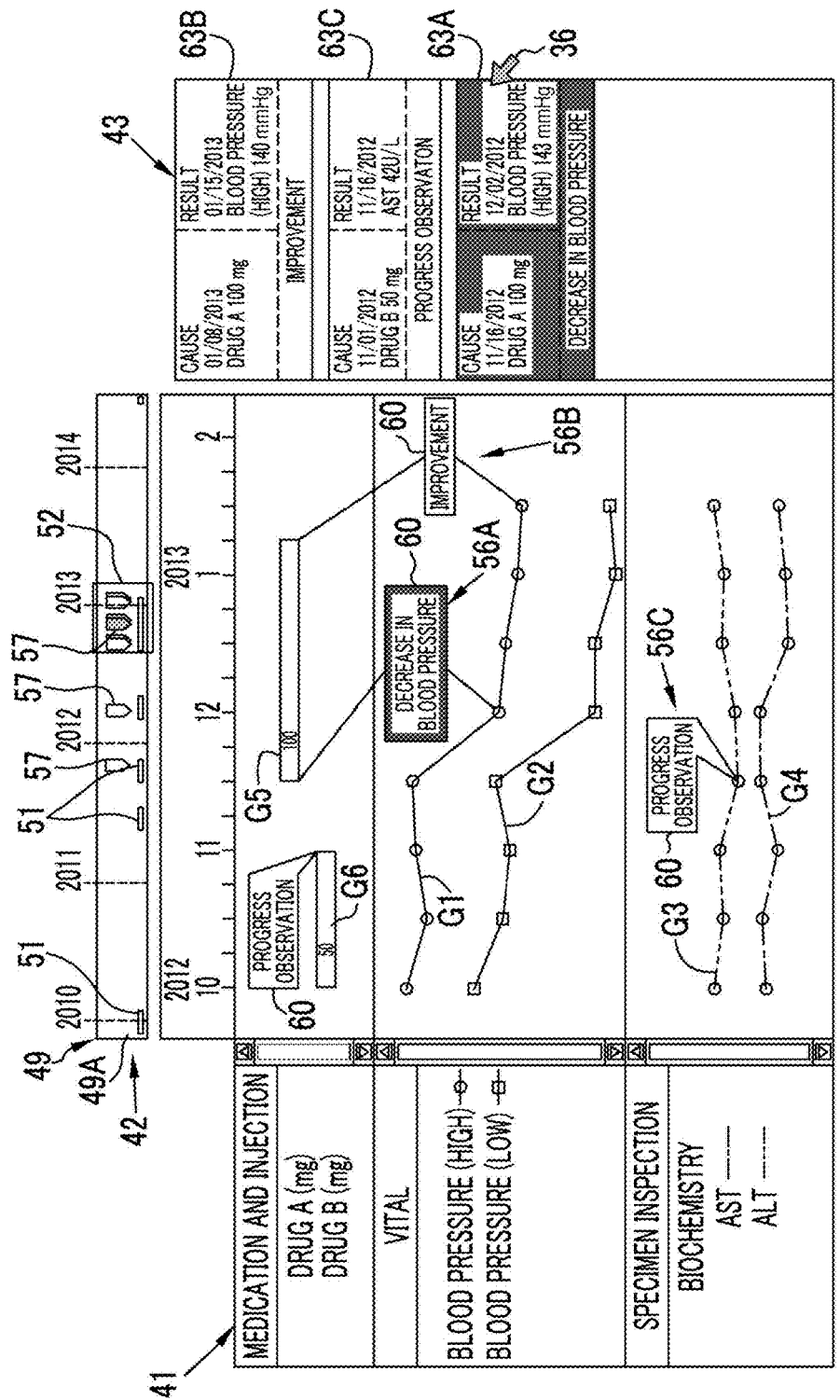
FIG. 14 is a diagram illustrating an example in which an association indicator and a corresponding indicator corresponding to set information in the list display area are displayed to be distinguishable by selection of the set information.

Further, as illustrated in FIG. 14, assuming that one piece of set information 63 is selected in the list display area 43, the association indicator 56 and the corresponding indicator 57 corresponding to the selected set information 63 may be displayed to be identifiable. Specifically, in the event that one of piece of set information 63 is selected by the pointer 36, the selected set information 63 and the association indicator 56 corresponding thereto in the first display area 41 are highlighted. Accordingly, the highlighted set information 63 and the other set information 63 are displayed to be identifiable in the list display area 43, and the highlighted association indicator 56 and other association indicators 56 are displayed to be identifiable in the first display area 41. Further, the corresponding indicator 57 corresponding to the selected set information 63 is highlighted in the second display area 42. Accordingly, the highlighted corresponding indicator 57 and other corresponding indicators 57 are displayed to be identifiable in the second display area 42.

On the other hand, in a case in which one association indicator 56 is selected in the first display area 41, one piece of set information 63 corresponding to the selected association indicator 56 and the corresponding indicator 57 in the second display area 42 may be displayed to be identifiable in the list display area 43. Thus, it is possible to simply confirm content of interest in the list display area 43 or the first display area 41 or the time in each other's areas. It should be understood that, in a case in which one the corresponding indicator 57 is selected in the second display area 42, one association indicator 56 corresponding to the selected corresponding indicator 57 and the set information 63 in the list display area 43 may be displayed to be identifiable.

Figure 15:
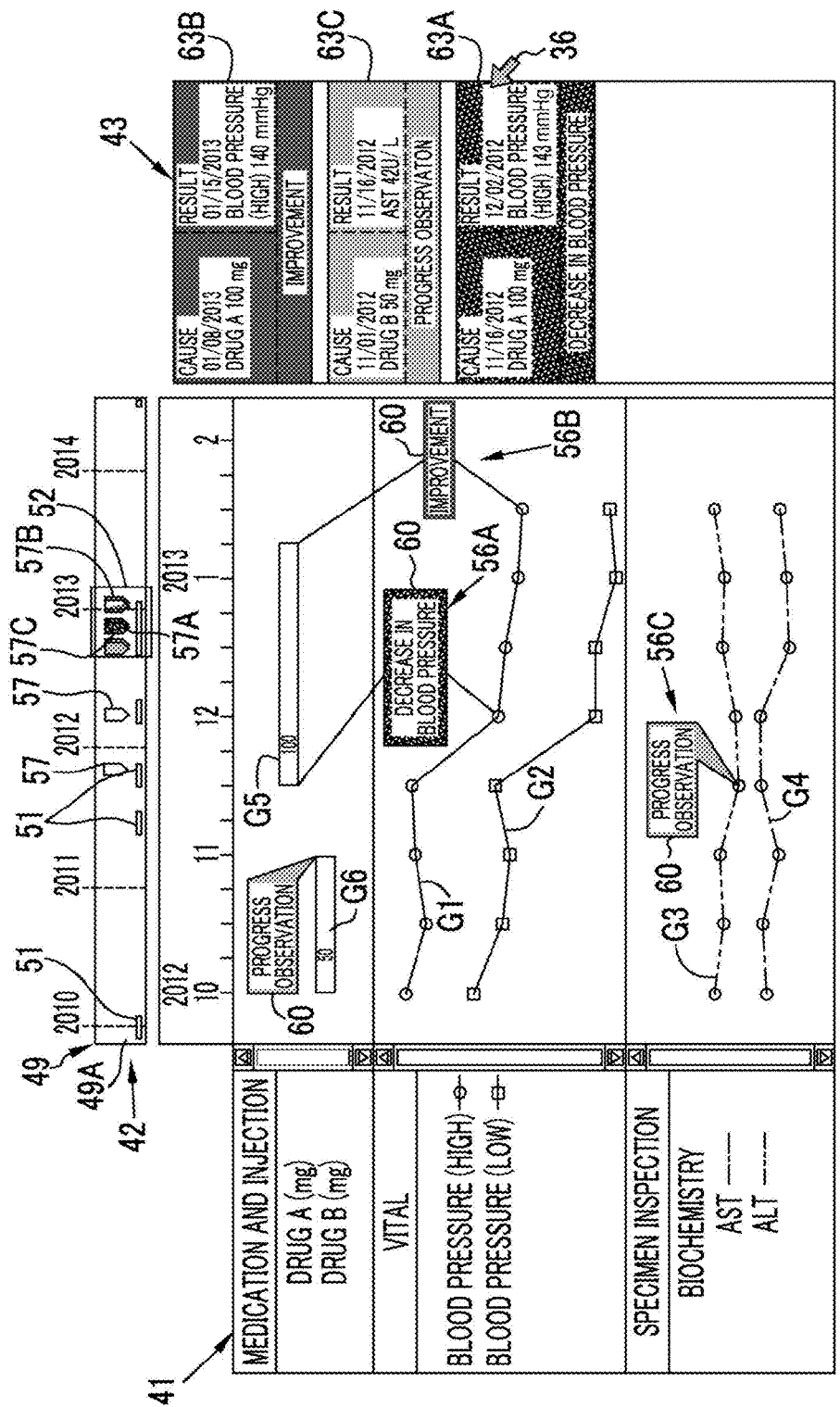
FIG. 15 is a diagram illustrating an example in which an association indicator and a corresponding indicator corresponding to each piece of set information in the list display area are displayed to be distinguishable.

Further, displays of the first display area 41, the second display area 42, and the list display area 43 may be in conjunction with one another as illustrated in FIG. 15. Assuming that there are a plurality of association indicators 56, a plurality of corresponding indicators 57 are displayed in the second display area 42, and a plurality of pieces of set information 63 are displayed in the list display area 43. In this case, since there are a plurality of sets of corresponding indicator 57 and set information 63 that are in a correspondence relationship, it is preferable that the correspondence relationship of each set can be confirmed at a glance by each set being identified and displayed.

In FIG. 15, by changing color of each set, for example, setting color of the set information 63A and the corresponding indicator 57A to "blue", color of the set information 63B and the corresponding indicator 57B to "red", and color of the set information 63C and the corresponding indicator 57C to "green", each set can be identified. Further, as in this example, for the association indicators 56A to 56C in the first display area 41, color may be changed corresponding to each set. Each set may be identified by a type of hatching, light and shade of the color, or the like, in addition to the color. Further, for example, the number of marks such as asterisks may be changed for each set so that each set can be identified.

Further, assuming that the number of association indicators 56 increases, it is difficult for the first display area 41 to be seen, as described above. Therefore, all the association indicator 56 in the first display area 41 are hidden in the initial state, and in a case in which the set information 63 in the list display area 43 is selected, the association indicator 56 corresponding to the set information 63 may be displayed. The selection of set information 63 is performed by, for example, a click operation using the pointer 36 or by a mouse-over operation for superimposing the pointer 36 on the set information 63 without performing the click operation.

Second Embodiment

Figure 16:
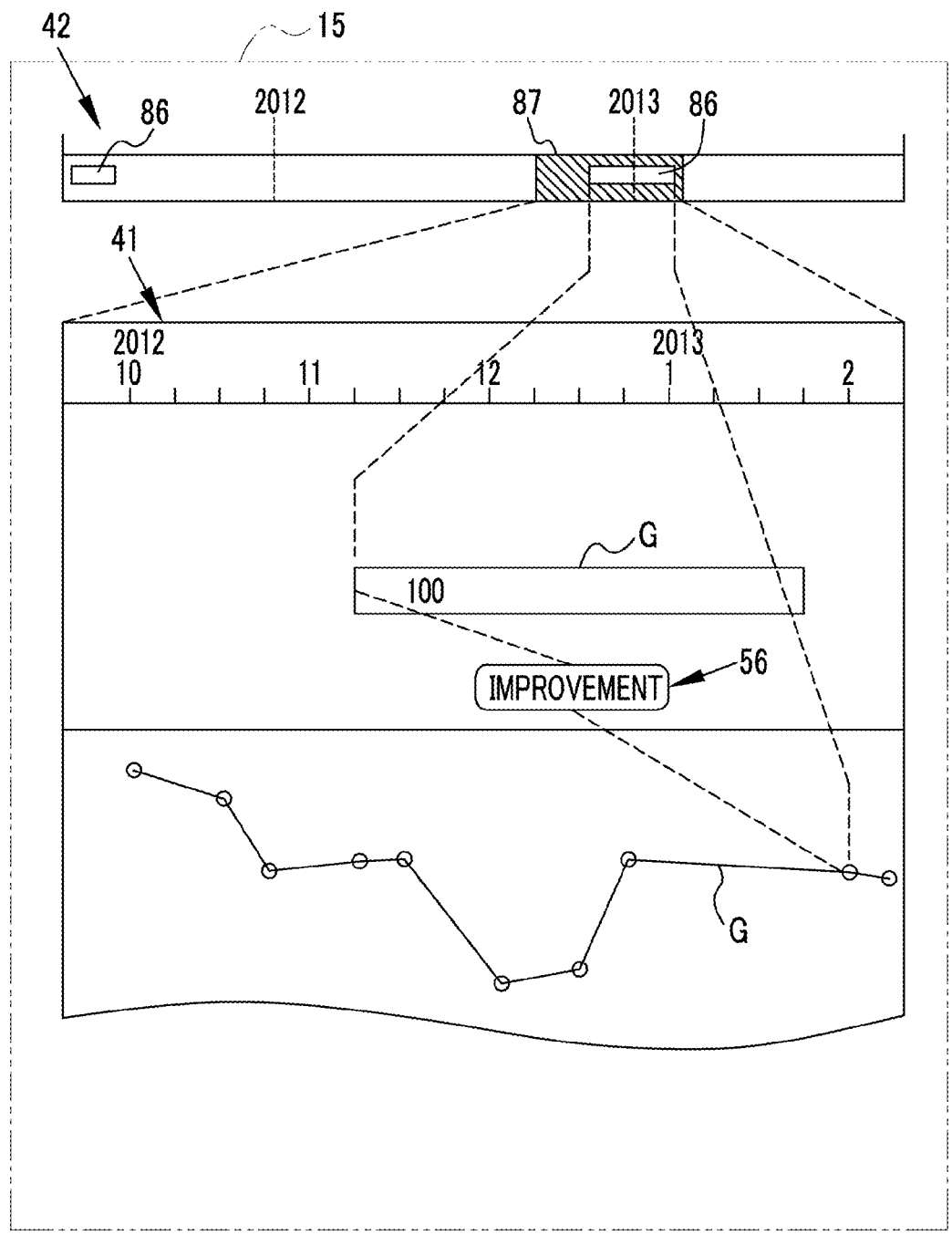
FIG. 16 is a diagram illustrating a display example of a corresponding indicator in a second embodiment.

As in a second embodiment illustrated in FIG. 16, in a case in which the association indicator 56 is assigned, one indicator corresponding to a period between a plurality of designated positions of the cause position and result position may be assigned like the corresponding indicator 86 instead of separately assigning the corresponding indicator displayed in the second display area 42 at the cause position and result position. The corresponding indicator 86 is displayed on the second time axis 49. In the second embodiment, a marker 87 is displayed as a period indicator having different color from that of other portions at the position of the first display period in the second display area 42.

Third Embodiment

Figure 17:
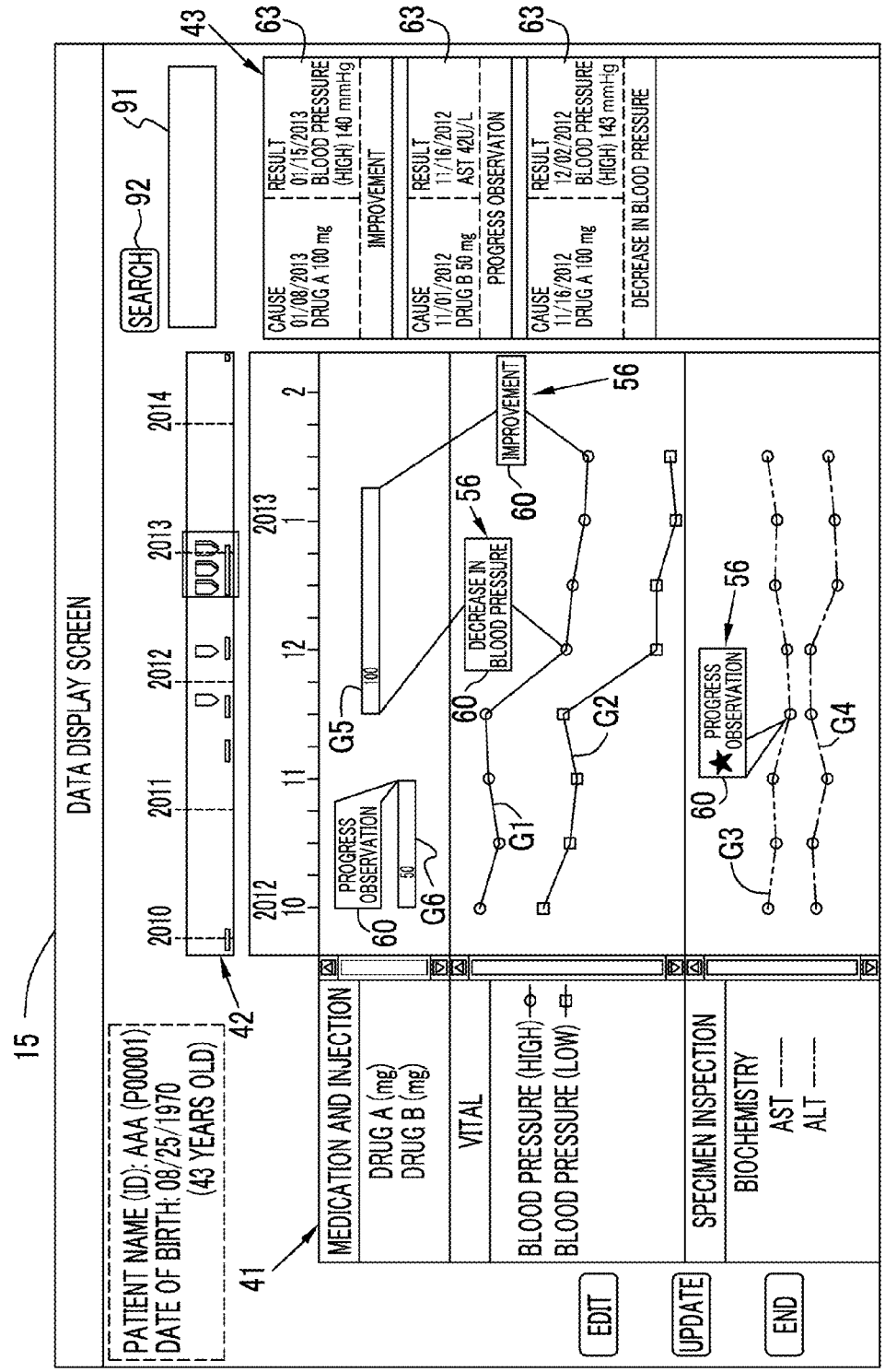
FIG. 17 is a diagram illustrating a data display screen of a third embodiment in which set information is searched for and displayed.
Figure 18:
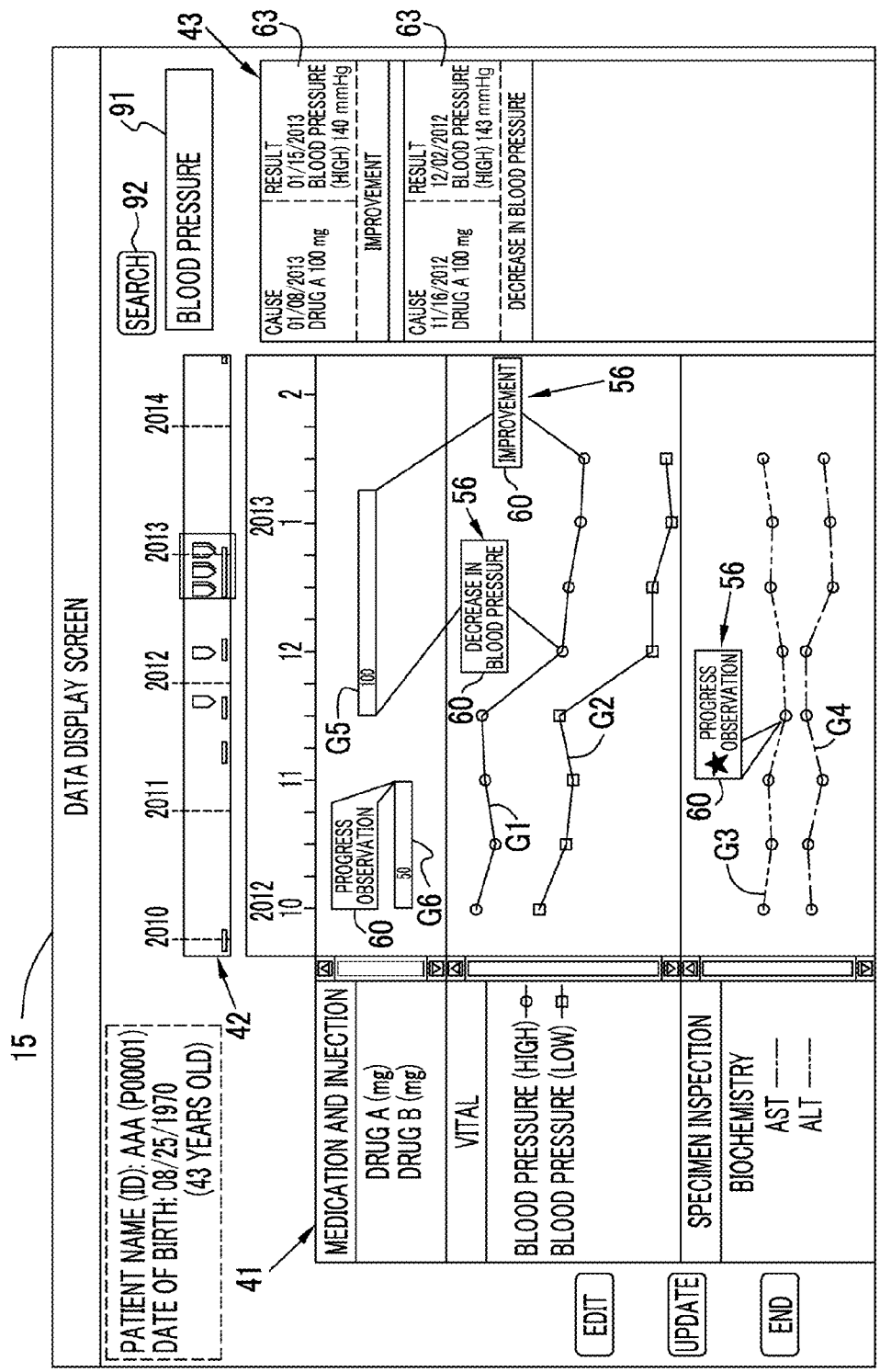
FIG. 18 is an illustrative diagram illustrating an example of a data display screen in a state in which some of the set information is hidden.

In a data display screen 15 of a third embodiment illustrated in FIGS. 17 and 18, a function of searching for set information 63 using a keyword is provided. Set information 63 extracted by the search is displayed in the list display area 43. As illustrated in FIG. 2, the individual data includes the information on the attribute. Since the set information 63 includes the individual data, keyword search of the set information 63 can be performed using the attributes of the individual data.

For example, as illustrated in FIG. 17, for example, assuming that "blood pressure" is input as a keyword in a state in which three pieces of set information 63 are displayed, the set information 63 including "blood pressure" in the attribute is extracted and, only two extracted pieces of set information 63 are displayed in the list display area 43, as illustrated in FIG. 18. In this example, a display of the first display area 41 is changed to a display of only the association indicator 56 corresponding to the extracted set information 63 in conjunction with the display of the list display area 43. Accordingly, it is possible to simply confirm the set information 63 or the association indicator 56 desired to be confirmed by the doctor.

A keyword input field 91 is an input field for inputting a keyword for searching for the set information 63. Assuming that the keyword is input and a search button 92 is operated, the GUI control unit 33 searches for the set information 63 included in the received screen data 15A. The GUI control unit 33 extracts the set information 63 having the attribute matching the input keyword from among items pieces of individual data that respective pieces of set information 63 have. In the list display area 43, the extracted set information 63 is displayed, and a display of the first display area 41 is changed in conjunction with the display of the list display area 43.

In the example of FIGS. 17 and 18, a search range of the set information 63 includes the set information 63 displayed in the list display area 43, it should be understood that the search range of the set information 63 is not limited to the set information 63 displayed in the list display area 43, and it is preferable for the search range of the set information 63 to include all of the set information 63 corresponding to the patient ID. In this case, since all of the set information 63 is highly likely not to be included in the screen data 15A received by the client terminal 12, the client terminal 12 in this case requests the data distribution server 11 to distribute additional set information 63. Alternatively, a method of causing the data distribution server 11 to execute a search process for set information 63 in response to a search request from the client terminal 12 and receiving a distribution of a search result may be used. Further, it is also preferable to display, for example, a list of attributes and a selection button corresponding thereto and select the attribute of the first indicator 96 of which the information is displayed in the content display field from the list, instead of inputting a keyword.

Fourth Embodiment

Figure 19:
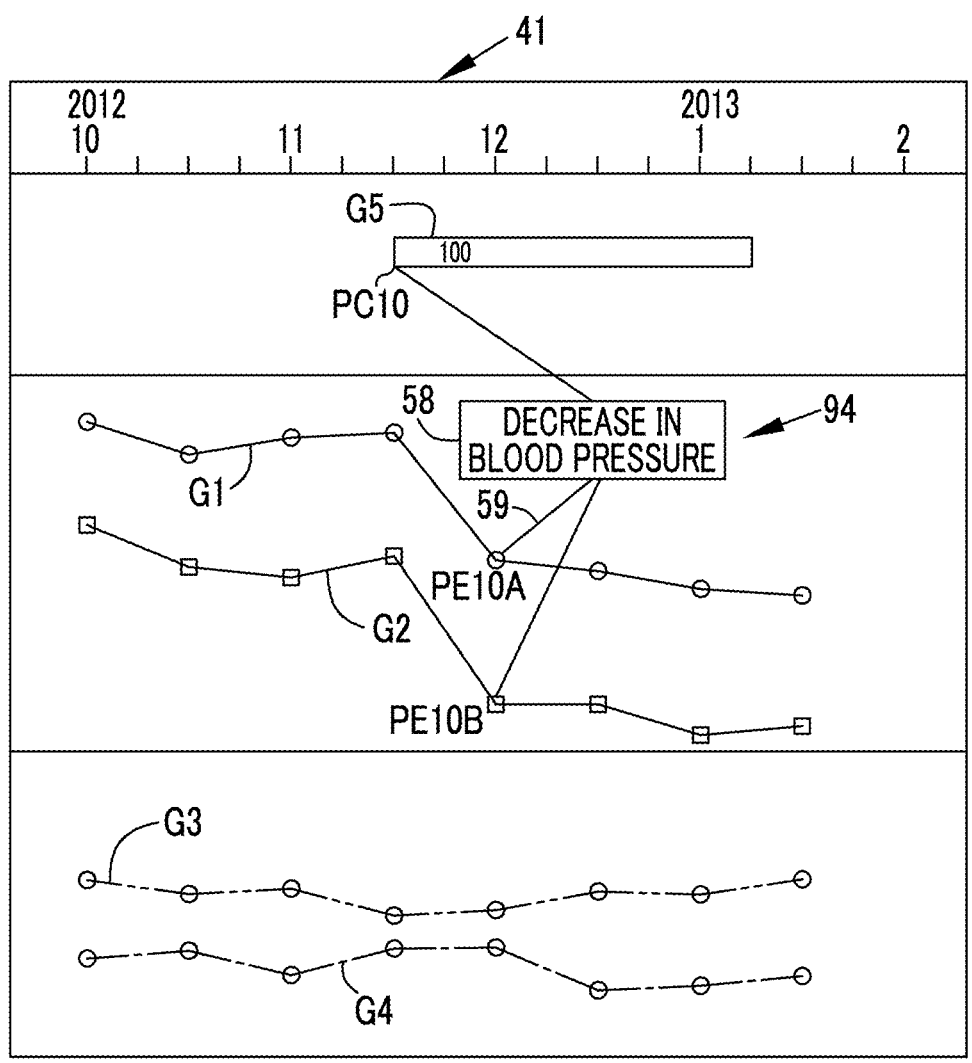
FIG. 19 is an illustrative diagram illustrating an example in which two result positions of an association indicator are set in a fourth embodiment.
Figure 20:
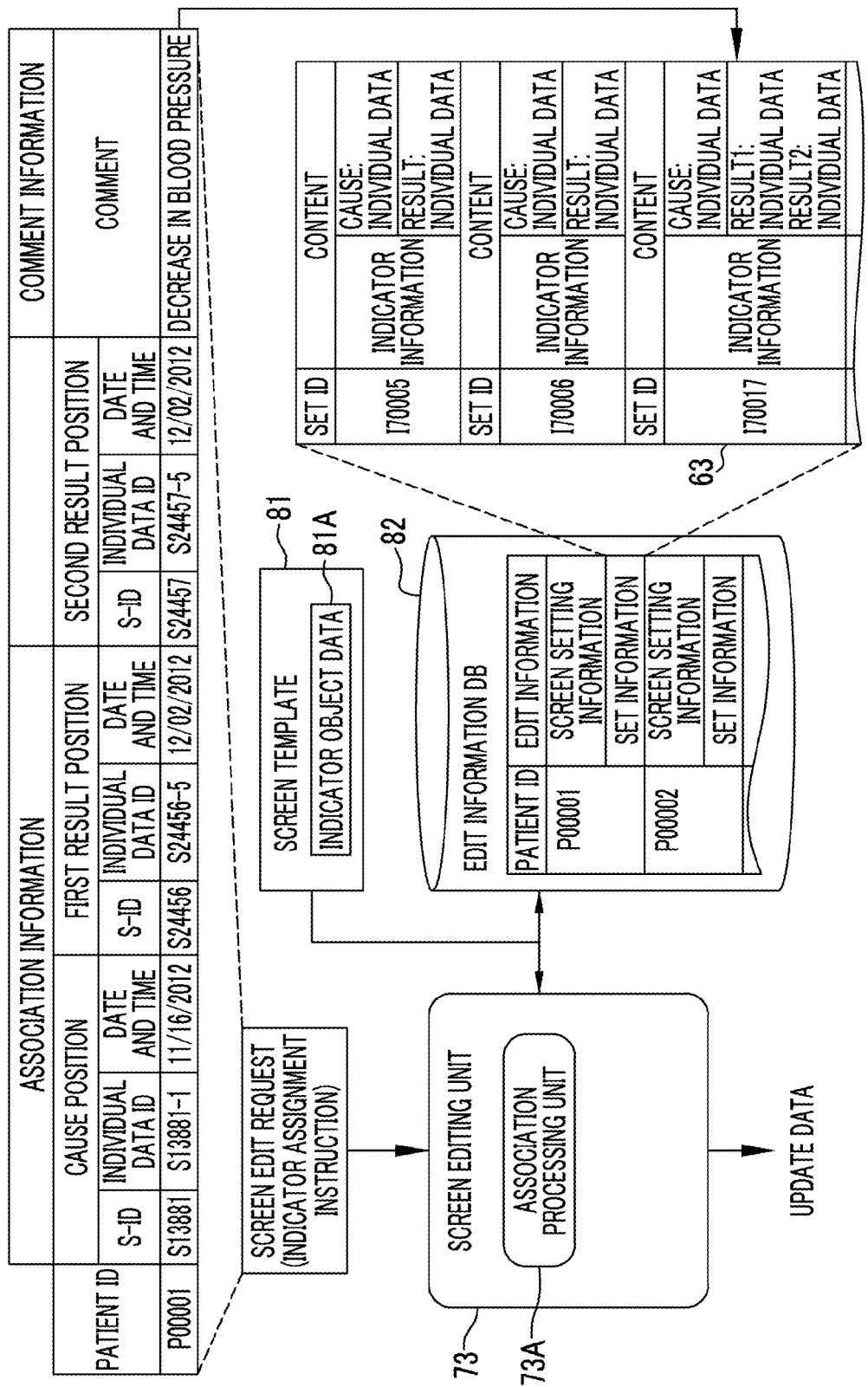
FIG. 20 is an illustrative diagram illustrating a schematic function of a screen editing unit regarding association indicator assignment in the fourth embodiment.

A fourth embodiment illustrated in FIGS. 19 and 20 is an example in which designated positions of the association indicator 94 include three designated positions. For example, any one of the cause position and the result position includes two positions. In this example, two result positions PE10A and PE10B are designated for one cause position PC10. The association indicator 94 can show a causal relationship between the plurality of results for one cause by means of such an association indicator 94. In this case, as illustrated in FIG. 20, information on one cause position and first and second result positions is included in the indicator assignment instruction. Correspondingly, one item of individual data corresponding to the cause position and two separate items of data corresponding to the two result positions are included in the set information 63. Contrary to this example, one result position may be designated for a plurality of cause positions. Further, although the example in which there are three designated positions has been described in this embodiment, the number of designated positions may 4 or more as long as a correspondence relationship between the cause and the result is one-to-many or many-to-one.

Fifth Embodiment

Figure 21:
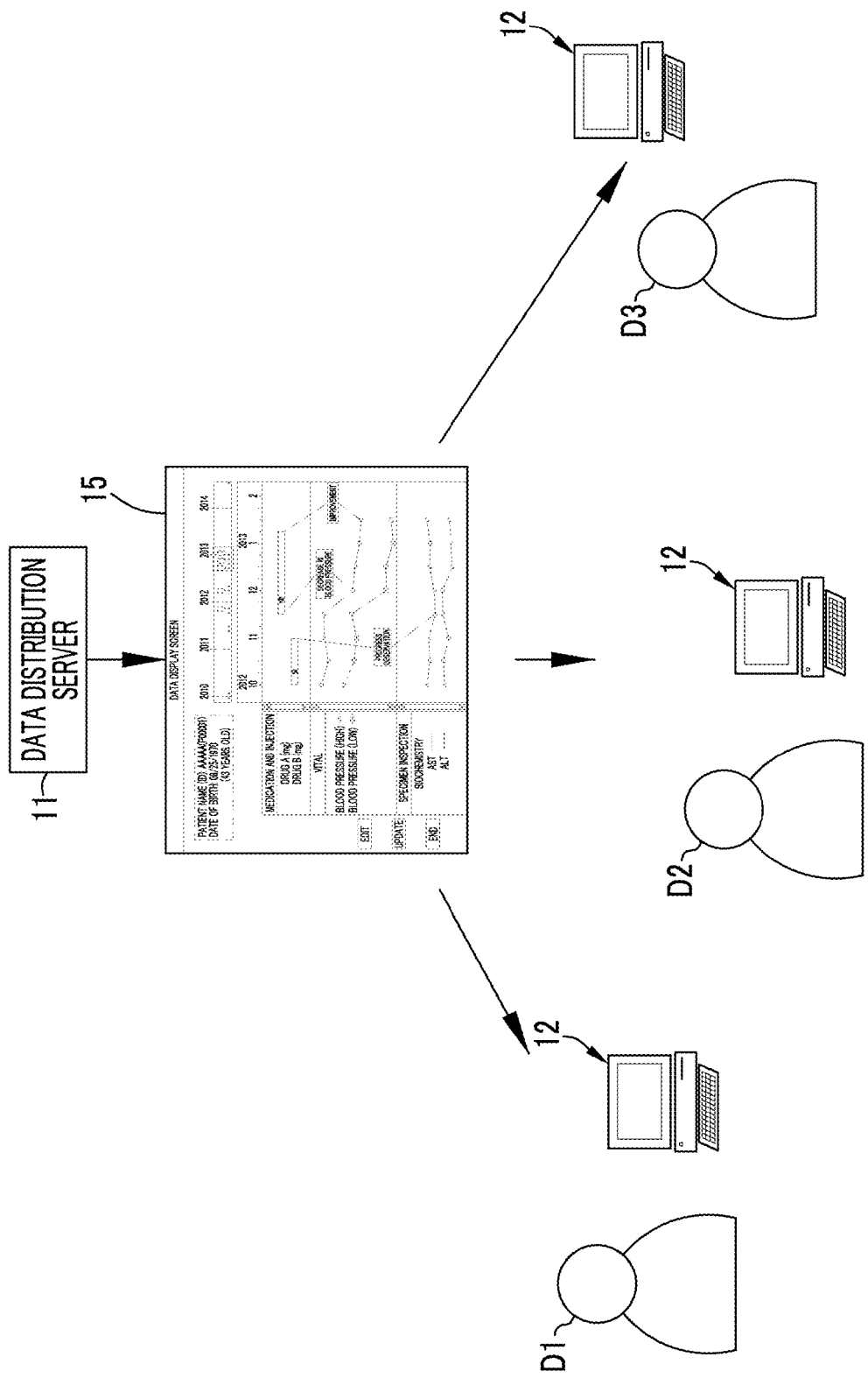
FIG. 21 is an illustrative diagram illustrating a conference of a sixth embodiment in which a grouping function is provided in a data distribution server.

A fifth embodiment illustrated in FIGS. 21 to 24 is an embodiment in which a function of grouping a plurality of set information 63 is provided in the data distribution server 11. As illustrated in FIG. 21, the data distribution server 11 having the grouping function is used, for example, for a conference in which a plurality of people examine a medical care plan for a patient. In the conference, a plurality of doctors D1 to D3 access the data distribution server 11 using respective client terminals 12 and view the same data display screen 15 at the same time. Time-series data TS for a certain patient is shared among the respective doctors D1 to D3, communication is collected, and the examination of the medical care plan is performed.

The conference is a use form of a computer system and is close to a so-called WEB conference. The data distribution server 11 can distribute the same data display screen 15 to a plurality of client terminals 12. In a case in which the data display screen 15 is updated according to a screen editing request from each client terminal 12, the update data is transmitted to other client terminals 12 and the data display screen 15 is synchronized among the respective client terminals 12. An authority of screen editing is limited to, for example, one client terminal 12 which is a conference organizer.

In the conference, a plurality of causal relationships among a plurality of items of time-series data TS are discussed by the respective doctors D1 to D3, and logical verification are collected, and an appropriate medical care plan is determined for a patient. A process of such a discussion corresponds to a flow of a logic leading to the appropriate medical care plan. Accordingly, assuming that this can be simply stored, it is very convenient in the event that the process of discussion is looked back later. Since the set information 63 indicates the causal relationship of the time-series data TS, a plurality of set information 63 which is a target of the discussion in the conference has a value corresponding to a gist of the flow of discussion. By using the grouping function of the data distribution server 11, it is possible to simply perform work of summarizing a plurality of sets information 63 which are targets of the discussion.

Figure 22:
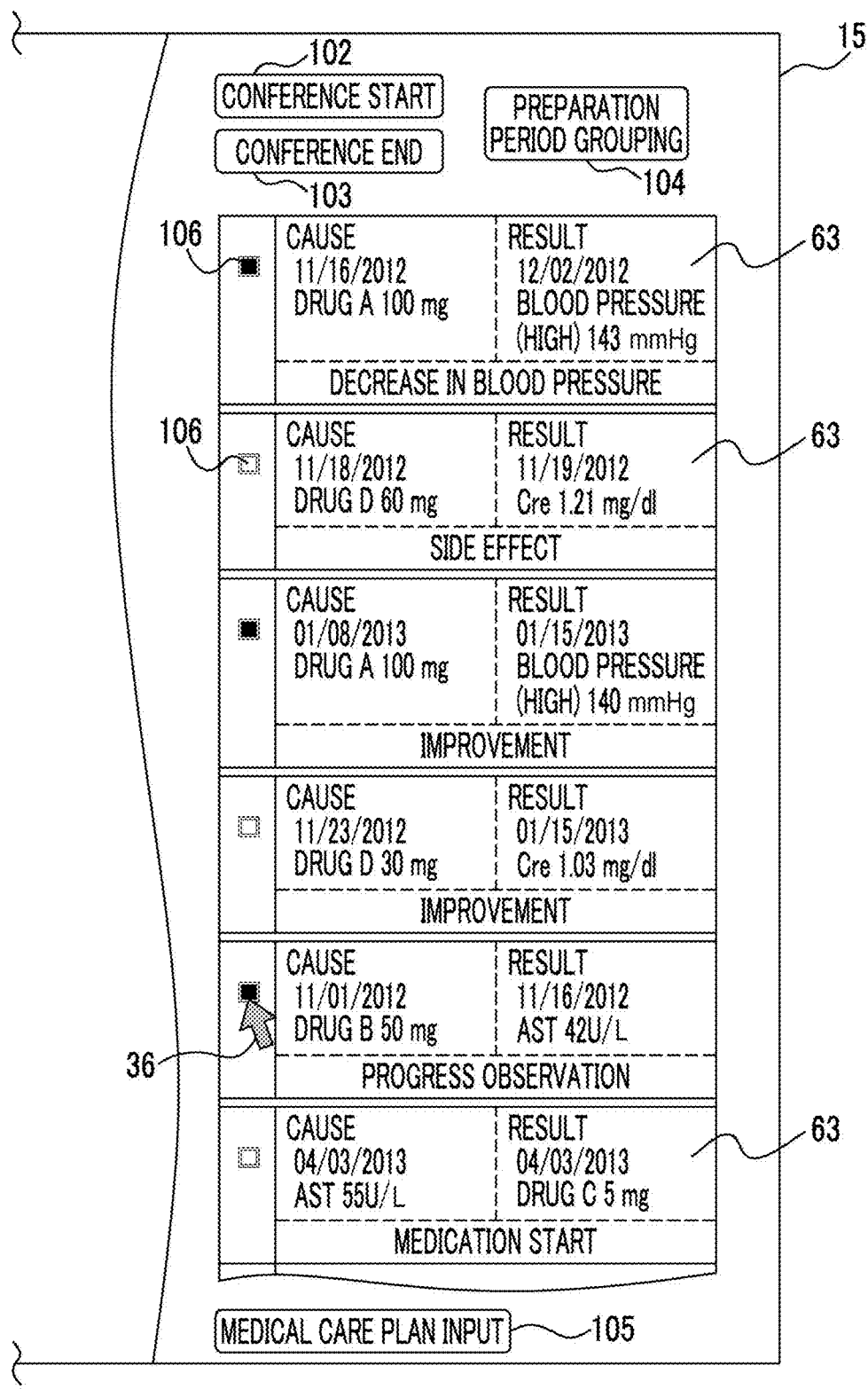
FIG. 22 is an illustrative diagram illustrating a screen for selecting the set information to be grouped.

As illustrated in FIG. 22, for example, a conference start button 102, a conference end button 103, a preparation period grouping button (hereinafter referred to as a preparation period button) 104, and a medical care plan input button 105 are provided in the data display screen 15 distributed by the data distribution server 11 with the grouping function. The data distribution server 11 groups a plurality of created or accessed set information 63 between a time at which the conference start button 102 is operated and a time at which the conference end button 103 is operated. A grouping instruction is transmitted to the data distribution server 11 by an operation of the conference start button 102, and the grouping end instruction is transmitted by an operation of the conference end button 103.

A check box 106 is provided next to each piece of set information 63. Assuming that the check box 106 is checked, access information indicating that the set information 63 has been accessed is transmitted to the data distribution server 11. The data distribution server 11 performs grouping on the basis of the access information, in addition to the newly created set information 63.

Further, the preparation period button 104 is an operation button for grouping the created or accessed set information 63 in a preparation period before the conference starts. The preparation period button 104 is activated with one click operation. Assuming that the preparation period button 104 is activated, a grouping instruction is transmitted to the data distribution server 11. In the event that the preparation period button 104 is clicked again, the preparation period button 104 is deactivated. Assuming that the preparation period button 104 is deactivated, the grouping end instruction is transmitted. The created or accessed set information 63 is grouped while the preparation period button 104 is being activated.

The medical care plan input button 105 is an operation button for inputting a medical care plan determined finally in a conference. Assuming that the medical care plan input button 105 is input, an input screen (not illustrated) is opened. The medical care plan input in the input screen is stored as grouping information.

Figure 23:
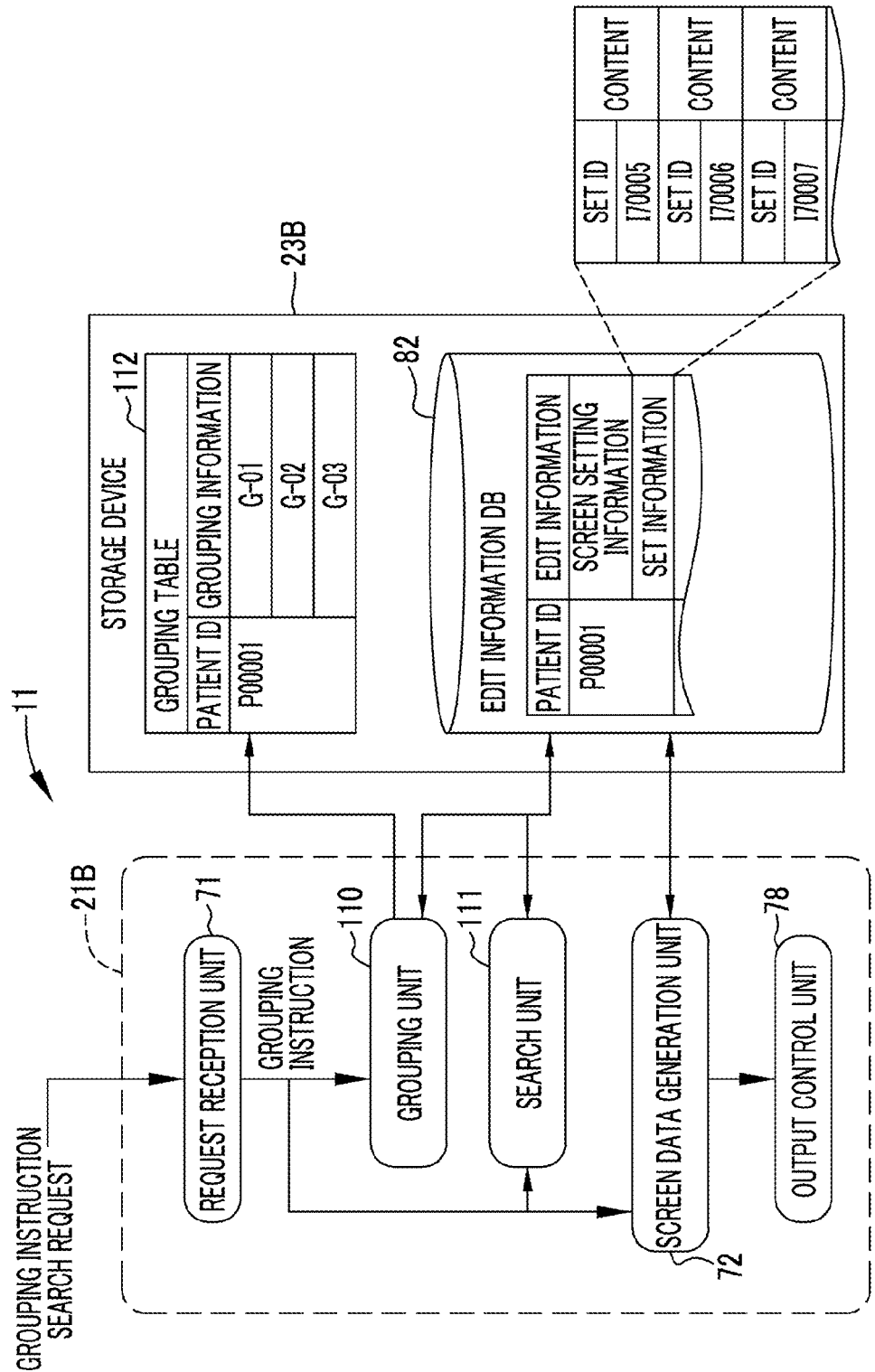
FIG. 23 is an illustrative diagram illustrating a schematic function of a data distribution server regarding grouping.

As illustrated in FIG. 23, the CPU 21B of the data distribution server 11 in this example functions as a grouping unit 110 and a search unit 111, in addition to, for example, the screen data generation unit 72. The grouping instruction received by the request reception unit 71 is input to the grouping unit 110. A grouping table 112 in which the grouping information is stored in units of patient IDs is included in the storage device 23E. Assuming that the grouping instruction is input, the grouping unit 110 monitors access information from the operation of the check box 106, and the indicator assignment instruction corresponding to a new creation instruction for the set information 63. Assuming that there is the access information or the indicator assignment instruction, the grouping unit 110 records the access information or the indicator assignment instruction in the grouping table 112 as an access history.

Figure 24:
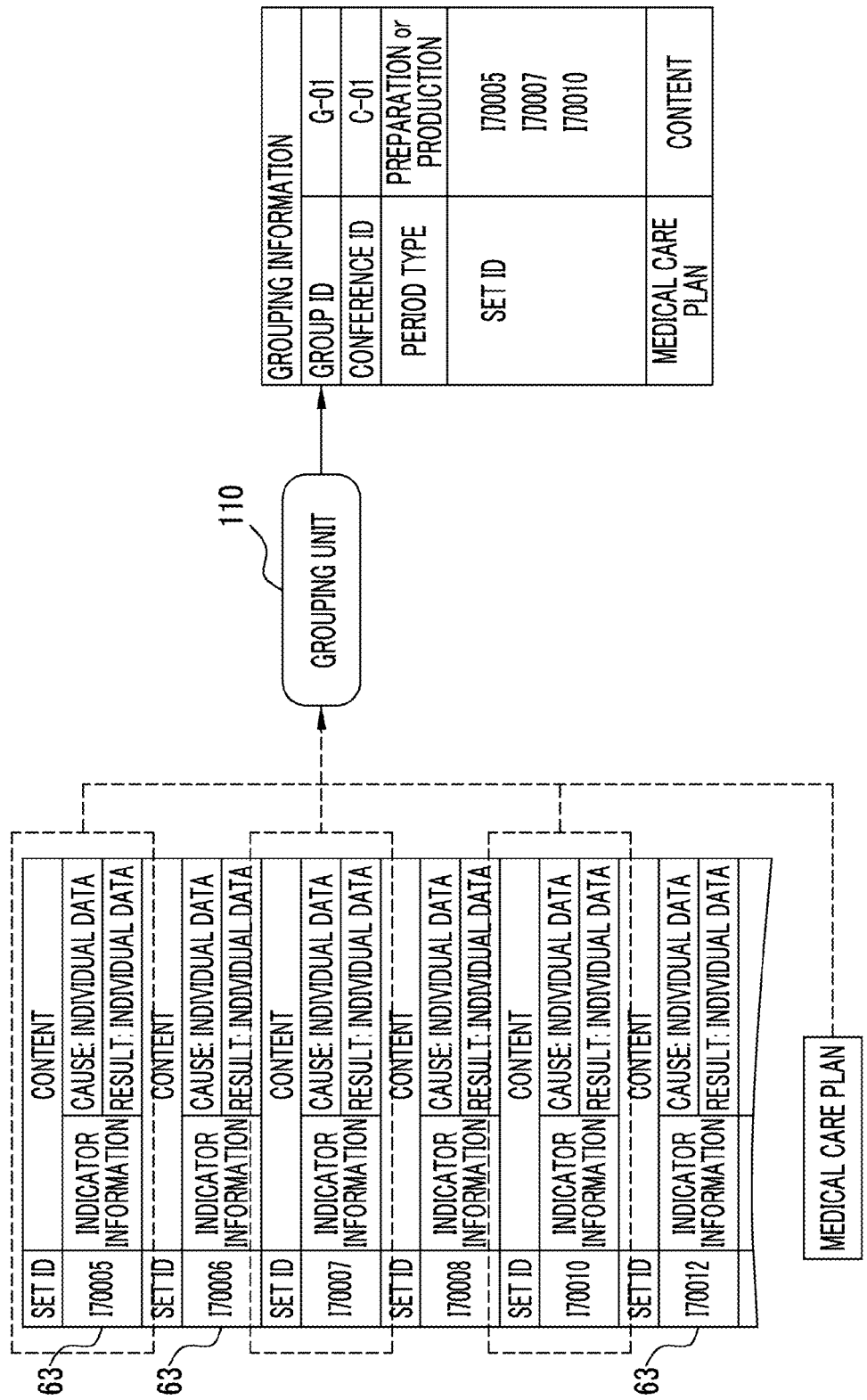
FIG. 24 is an illustrative diagram illustrating generation of grouping information in a grouping unit.

As illustrated in FIG. 24, the grouping unit 110 collects a data set including a plurality of pieces of set information 63 that are newly created or accessed during the conference, as one group, and stores the group as grouping information. An ID is assigned to the grouping information in units of conferences. Further, the conference period may include a preparation period in which preparation for a production period is performed, in addition to the production period in which the conference is actually performed. In this case, a period type for identifying whether the group to be created is for the set information 63 newly created or accessed in the production period of the conference or for the set information 63 newly created or accessed in the preparation period of the conference is also included in the grouping information, as illustrated in FIG. 24. The set ID is stored with creation date and time or access date and time. Here, the set information newly created or accessed in the production period corresponds to first set information, and the set information newly created or accessed in the preparation period corresponds to second set information.

The searching unit 111 receives a search key such as a group ID from the client terminal 12 and searches for the group information that is a set of a plurality of pieces of set information 63. Accordingly, the grouping information in a conference unit can be distributed to the client terminal 12. In the client terminal 12, a plurality of pieces of set information 63 included in the distributed grouping information are displayed in, for example, the list display area 43. The plurality of pieces of set information 63 can be sorted in an order of creation or access and displayed. Therefore, it is possible to simply look back the process of discussion in the conference.

The grouping information includes not only the set information 63, but also information on a medical care plan finally determined in the conference. Since the conference is performed by the plurality of doctors D1 to D3, reliability of an examination result is high and a value as knowhow of diagnosis high. Accordingly, a discussion process or a finally determined medical care plan is very useful as support information for diagnosis. According to this example, it is possible to simply store such useful information.

Further, since not only the production period of the conference, but also the grouping information of the preparation period can be created, it is also possible to support preparation work of a conference organizer. Since a determination of the preparation period and a determination after conference end are stored, a difference therebetween can be verified later or can be referred to by doctors with different experience. Accordingly, this is very useful as information for education between doctors. Further, although the grouping information is created on the basis of the access history of the set information 63 in the production period and the preparation period of the conference in this example, the set information 63 stored as the grouping information may be manually designated regardless of the access history.

Figure 25:
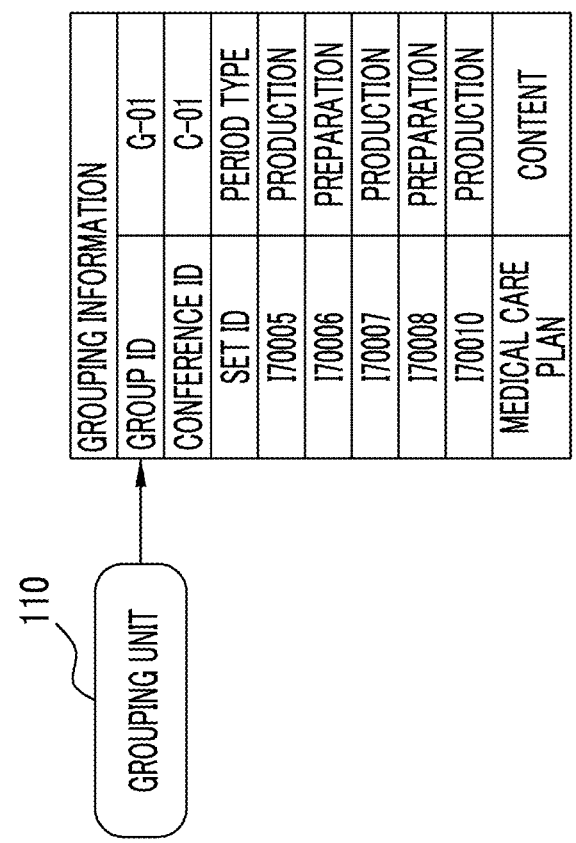
FIG. 25 is an illustrative diagram illustrating an example in which a set type is recorded in grouping information.

In the example illustrated in FIG. 24, for each group, the period type of any one of the production period and the preparation period is designated and the set information 63 of the production period and the set information 63 of the preparation period are collected in separate groups and stored. On the other hand, the grouping information in the example illustrated in FIG. 25 is stored in a form in which the respective pieces of set information 63 of the production period and the preparation period exist in one group. The group information may be stored in this form.

The grouping unit 110 records the period type for each set of information 63 according to whether a timing of new creation or access of the set information 63 is a production period or a preparation period of the conference. In the event that the grouping information is stored, the period type (or the production period or the preparation period) corresponding to each piece of set information 63 is associated and stored in the grouping information.

Further, although the example in which the grouping function in this example is used for the conference has been described, for example, the grouping function may be used for purposes other than the conference, like recording of a process of examination performed by one person.

Figure 26:
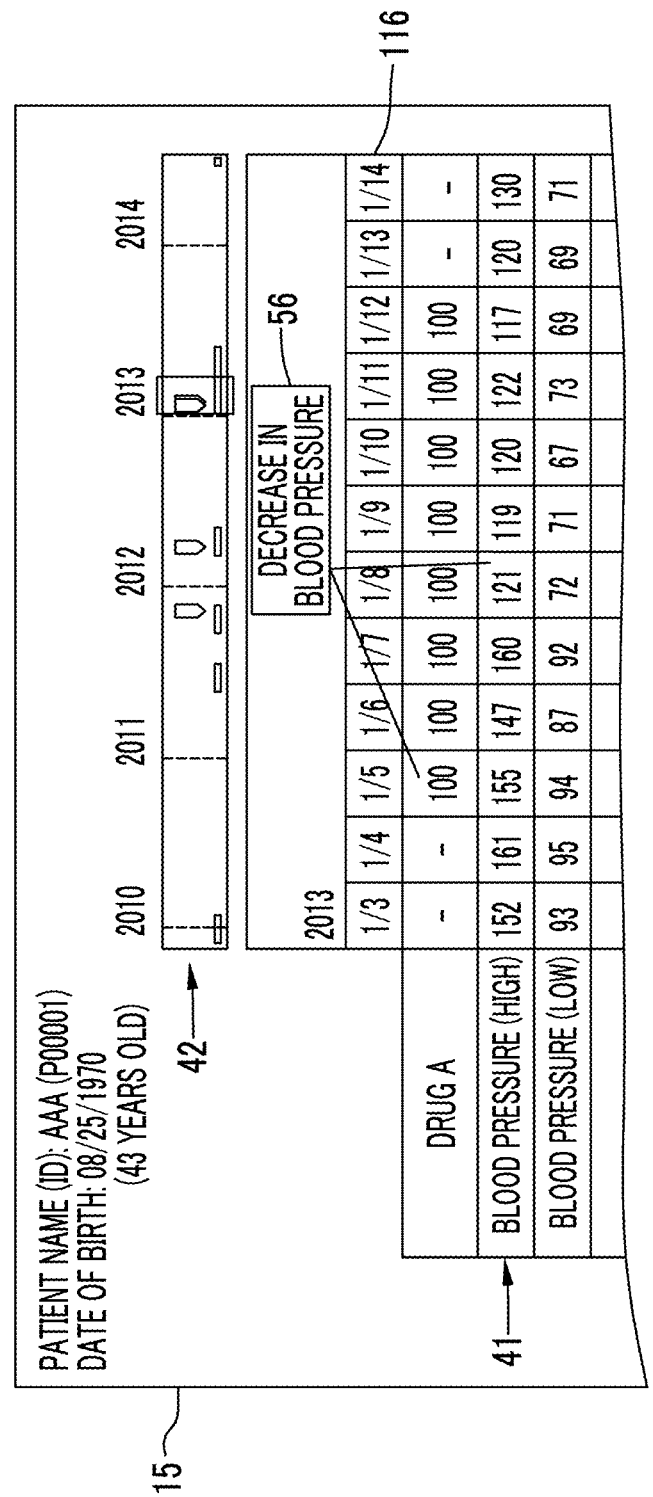
FIG. 26 is an illustrative diagram illustrating an example in which time-series data is displayed in a first display area in a table format.

Although the example in which the time-series data TS is displayed as a graph has been shown in each embodiment, the display form may be displayed in a table format, as illustrated in FIG. 26. In a table 116 in FIG. 26, respective pieces of time-series data TS of drug A, blood pressure (high) and blood pressure (low) are arranged in a vertical direction in a first display area 41 of a data display screen 15, and measured values that are individual data of each piece of time-series data TS are arranged in a horizontal direction in time series. An association indicator 56 may be assigned to the individual data or a cell of each piece of the individual data and displayed, as illustrated.

Although the example in which the first display area and the second display area are a plurality of areas assigned within one screen has been described in each embodiment, for example, the respective areas may be a plurality of separated independent display screens, like a multi-window format. In short, the first display area and the second display area may be in any format as long as the display areas can be displayed in parallel on a screen of a display.

Although the data output device of the present invention has been described as the form of the data distribution server 11 that distributes screen data of the data display screen on the basis of a request from the client terminal 12 in each embodiment, it should be understood that the client terminal 12 may be the data output device in place of the data distribution server 11. In this case, the client terminal 12 accesses the server group 13, acquires the time-series data, and generates the screen data of the data display screen. The client terminal 12 outputs the generated screen data to the display and displays the screen data on the display. In this case, the data output device may include the display.

Various modifications of a hardware configuration of a computer system such as the client terminal 12 or the data distribution server 11 can be made. For example, the storage device 23B provided in the data distribution server 11 and storing the edit information DB 82 or the screen template 81 may be a data storage device separate from the data distribution server 11. In this case, a RAM that temporarily stores the set information 63 may be provided in the data distribution server 11. In the data distribution server 11, the data storage device is accessed to store and read the edit information including the set information 63.

Further, for example, the data distribution server 11 can include a plurality of server computers separated as hardware in order to improve processing capacity or reliability. Thus, the hardware configuration of the computer system can be appropriately changed according to required performance, such as processing capability, safety, and reliability. Further, it should be understood that a program such as the edit information DB 82 or the AP 30, as well as the hardware, can be made redundant or can be distributed and stored in a plurality of storage devices in order to ensure safety or reliability.

Further, although the data distribution server 11 has been described in a form that the data distribution server 11 is used within one medical facility in each embodiment, the data distribution server 11 may be in a form in which the data distribution server 11 is available to a plurality of medical facilities.

Figure 27:
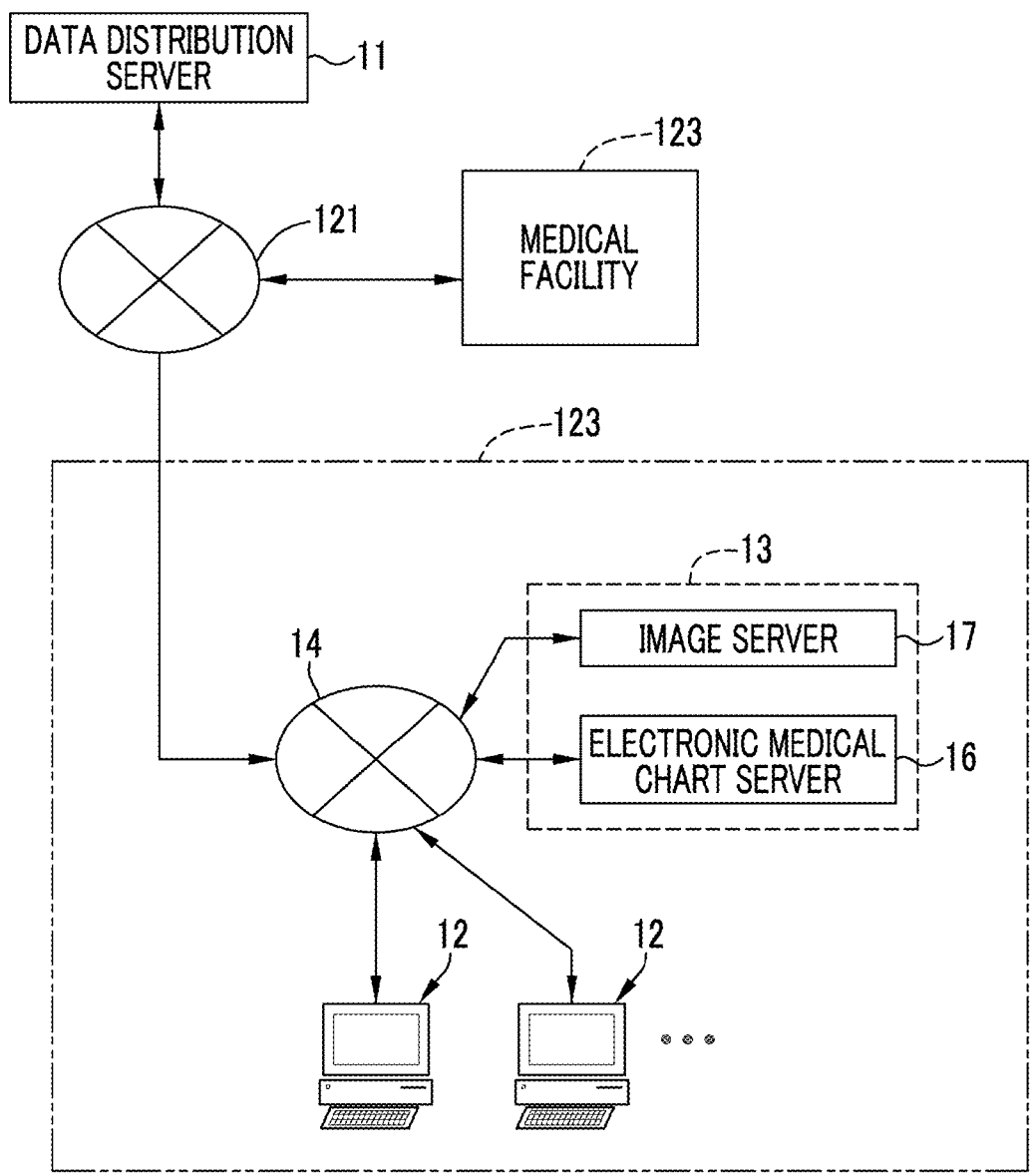
FIG. 27 is an illustrative diagram illustrating a configuration of a medical information management system in which a data distribution server is arranged outside a medical facility.

Specifically, in each embodiment, the data distribution server 11 is in the form in which the client terminal 12 installed in the one medical facility is connected to the data distribution server 11 to be able to communicate over the network 14 such as a LAN, and the data distribution server 11 provides an application service regarding the distribution of the screen data on the basis of the request from the client terminal 12. In order for the data distribution server 11 to be available to a plurality of medical facilities, for example, the data distribution server 11 is connected to be able to communicate with the client terminals 12 installed in the plurality of medical facilities 123, for example, over a Wide Area Network (WAN) 121 such as the Internet or a public communication network, as illustrated in FIG. 27. The data distribution server 11 receives the requests from the client terminals 12 in the plurality of medical facilities 123, and provides the application service regarding the distribution of the screen data to each client terminal.

An installation place or an operating subject of the data distribution server 11 in this case, for example, may be a data center different form the medical facility 123 or may be one of the plurality of medical facilities 123. Further, in a case in which a WAN is used, it is preferable that a Virtual Private Network (VPN) is constructed or a communications protocol having a high security level such as Hypertext Transfer Protocol Secure (HTTPS) is used in consideration of information security.

Figure 28:
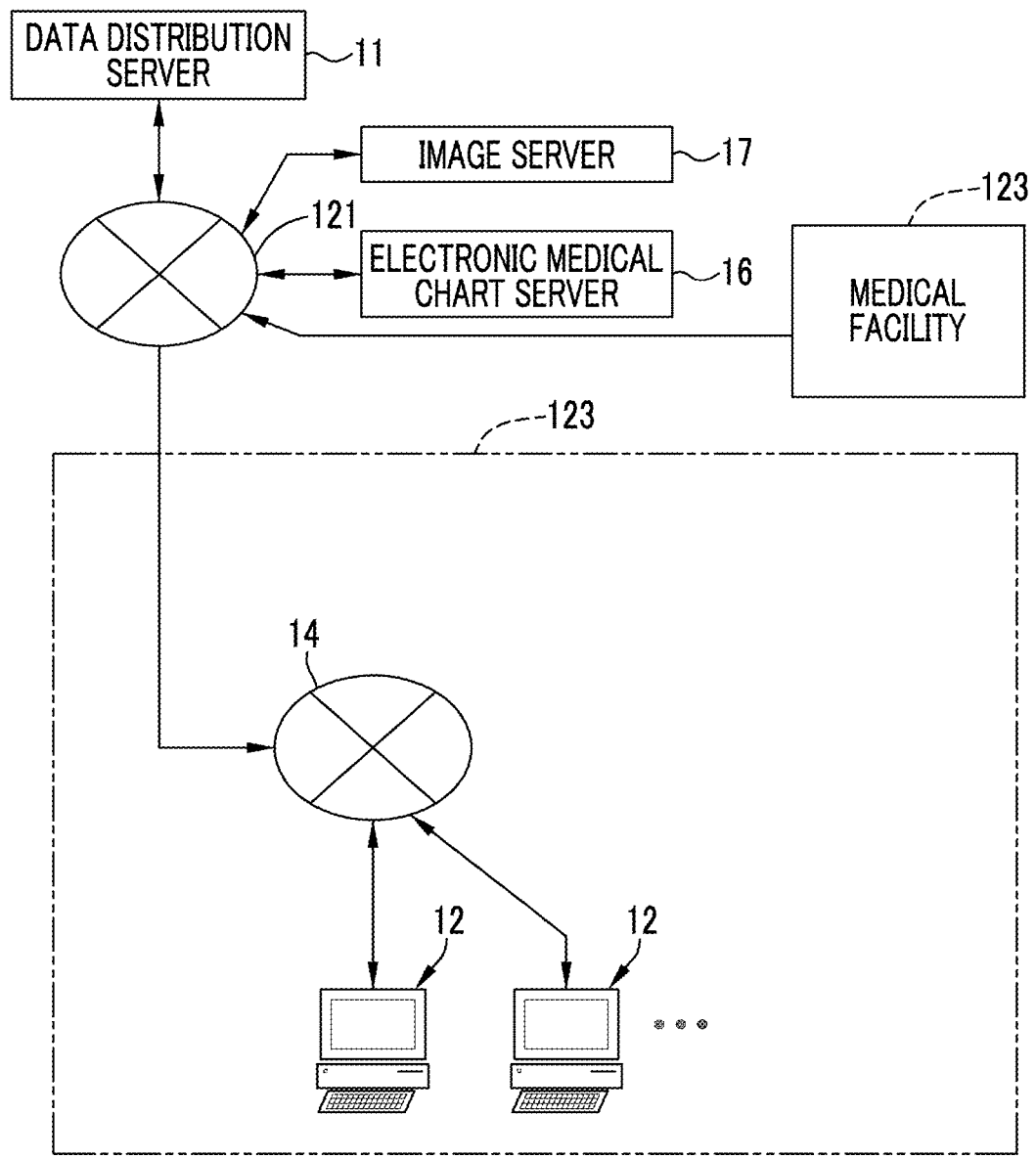
FIG. 28 is an illustrative diagram illustrating a configuration of a medical information system in which a data distribution server, an electronic medical chart server, and an inspection image server are arranged outside a medical facility.
Figure 29:
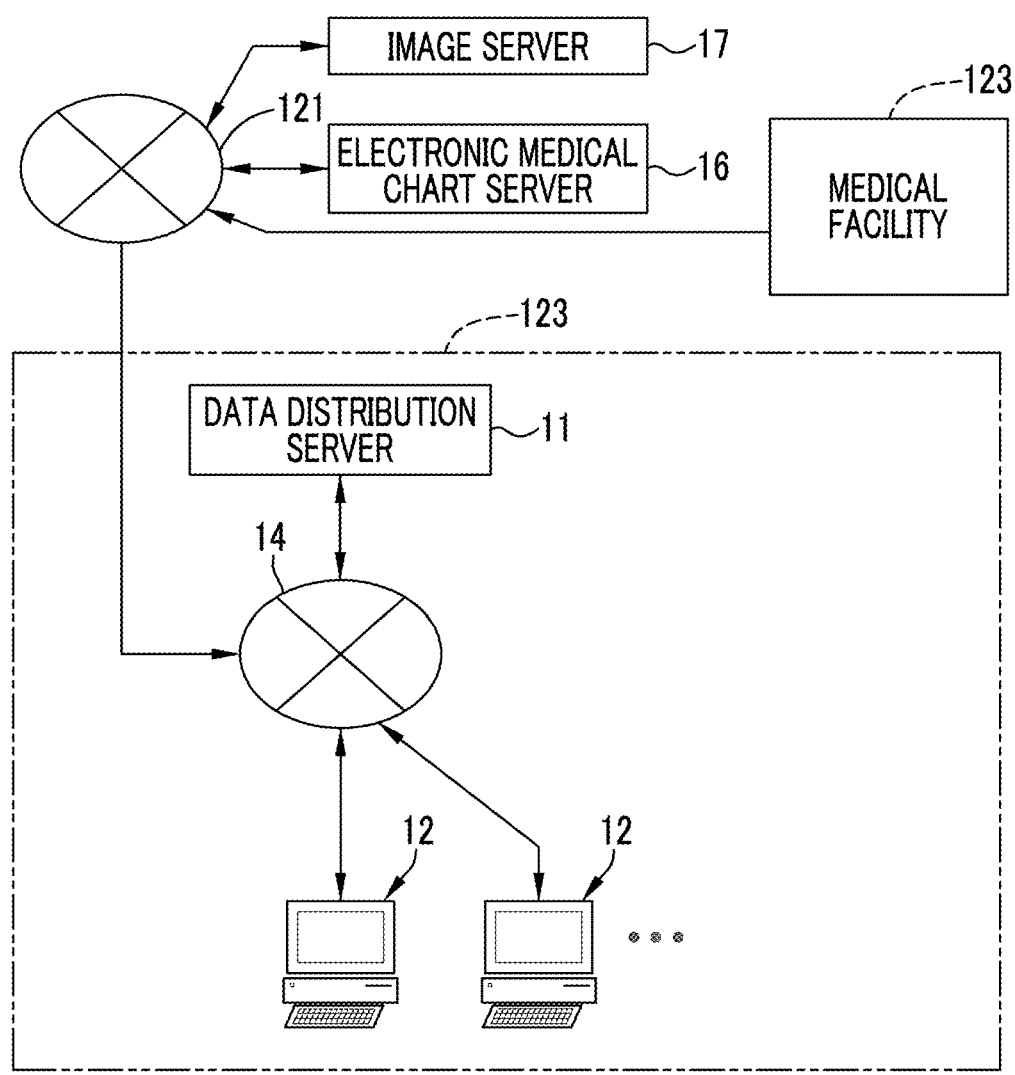
FIG. 29 is an illustrative diagram illustrating a configuration of a medical information management system in which a data distribution server is arranged in a medical facility, and an electronic medical chart server and an inspection image server are arranged outside the medical facility.

Further, as illustrated in FIG. 28, the electronic medical chart server 16 or the image server 17 may be installed outside the medical facility 123. As illustrated in FIG. 29, the data distribution server 11 may be installed within the medical facility 123 and only the electronic medical chart server 16 or the image server 17 installed in the outside may be used.

It should be understood that the present invention is not limited to each embodiment and various configurations may be adopted as long as the configurations depart from the gist of the present invention. For example, various embodiments or various modification examples described above may be appropriately combined. Further, the present invention includes a storage medium that stores the program, in addition to the program.

What is claimed is:

1. A data output device for displaying time-series data indicating at least one of a transition of a condition of a patient or content of medical care performed on the patient, the data output device comprising:
   a processor configured to:
   generate screen data of a data display screen for displaying at least two items of time-series data including first time-series data and second time-series data, the first and second time-series data representing temporal variations of different kinds of physical quantity from each other;
   receive an association instruction to associate an arbitrary first designated position in the first time-series data with an arbitrary second designated position in the second time-series data in a causal relationship; and
   assign an association indicator indicating that the first designated position and the second designated position are associated with each other in the causal relationship, in the data display screen, based on the association instruction,
   wherein the data display screen includes a first display area for displaying the first time-series data and the second time-series data, and a list display area for displaying a plurality of pieces of set information as a list,
   wherein each of the plurality of pieces of set information includes first information on the first designated position in the first time-series data, second information on the second designated position in the second time-series data, and an input comment, and
   wherein the list display area displays the first information, the second information and the input comment for each of the plurality of pieces of set information.

2. The data output device according to claim 1,
wherein the processor is further configured to store association information indicating that the first designated position and the second designated position are associated with each other in a storage unit.

3. The data output device according to claim 2,
wherein the association indicator includes a first indicator assigned at the first designated position, and a second indicator assigned at the second designated position.

4. The data output device according to claim 2,
wherein at least one of the first designated position or the second designated position is able to be designated as a plurality of positions.

5. The data output device according to claim 2,
wherein the processor is further configured to store information on the first designated position in the first time-series data, information on the second designated position in the second time-series data, and the association information, as one piece of set information, in the storage unit.

6. The data output device according to claim 5,
wherein the set information includes causal relationship information indicating that one of the information on the first designated position and the information on the second designated position is a cause, and the other is a result.

7. The data output device according to claim 5,
wherein the processor is further configured to add the input comment to the set information.

8. The data output device according to claim 7,
wherein the comment is displayed in the data display screen in addition to the association indicator or as the association indicator.

9. The data output device according to claim 1,
wherein in a case in which one piece of set information in the list display area is selected, the association indicator corresponding to the selected set information is displayed to be distinguishable in the first display area.

10. The data output device according to claim 1,
wherein in a case in which one association indicator in the first display area is selected, the set information corresponding to the selected association indicator is displayed to be identifiable in the list display area.

11. The data output device according to claim 1,
wherein the data display screen further includes a second display area for displaying a time axis at a relatively longer time scale than that of the first display area, and
a corresponding indicator indicating that there is the association indicator is displayed at a corresponding position corresponding to a period from the first designated position to the second designated position in the time axis in the second display area.

12. The data output device according to claim 11,
wherein in a case in which there are a plurality of sets of one piece of set information in the list display area and one corresponding indicator in the second display area corresponding to the set information, each set is displayed to be identifiable.

13. The data output device according to claim 1,
wherein an order of display of a plurality of pieces of set information is able to be changed in the list display area.

14. The data output device according to claim 13,
wherein the order of display of the set information is any one of an order of creation of the set information and an order of access to the set information.

15. The data output device according to claim 13, wherein the processor is further configured to group one or more pieces of set information.

16. The data output device according to claim 15,
wherein in a case in which the data display screen is used for a conference in which a medical care plan for a patient is examined by a plurality of persons,
the processor is further configured to collect and store a plurality of pieces of set information created or accessed during a period of the conference, in one group using one conference as a unit.

17. A data output method for displaying time-series data indicating at least one of a transition of a condition of a patient or content of medical care performed on the patient on a display unit, the data output method comprising:
generating screen data of a data display screen for displaying at least two items of time-series data including first time-series data and second time-series data, the first and second time-series data representing temporal variations of different kinds of physical quantity from each other;
receiving an association instruction to associate an arbitrary first designated position in the first time-series data with an arbitrary second designated position in the second time-series data in a causal relationship; and
assigning an association indicator indicating that the first designated position and the second designated position are associated with each other in the causal relationship, in the data display screen, based on the association instruction,
wherein the data display screen includes a first display area for displaying the first time-series data and the second time-series data, and a list display area for displaying a plurality of pieces of set information as a list,
wherein each of the plurality of pieces of set information includes first information on the first designated position in the first time-series data, second information on the second designated position in the second time-series data, and an input comment, and
wherein the list display area displays the first information, the second information and the input comment for each of the plurality of pieces of set information.

18. A non-transitory computer readable medium for storing a computer-executable program enabling execution of computer instructions to perform operations for displaying time-series data indicating at least one of a transition of a condition of a patient or content of medical care performed on the patient on a display unit, said operations comprising:
generating screen data of a data display screen for displaying at least two items of time-series data including first time-series data and second time-series data, the first and second time-series data representing temporal variations of different kinds of physical quantity from each other;
receiving an association instruction to associate an arbitrary first designated position in the first time-series data with an arbitrary second designated position in the second time-series data in a causal relationship; and
assigning an association indicator indicating that the first designated position and the second designated position are associated with each other in the causal relationship, in the data display screen, based on the association instruction,
wherein the data display screen includes a first display area for displaying the first time-series data and the second time-series data, and a list display area for displaying a plurality of pieces of set information as a list, wherein each of the plurality of pieces of set information includes first information on the first designated position in the first time-series data, second information on the second designated position in the second time-series data, and an input comment, and wherein the list display area displays the first information, the second information and the input comment for each of the plurality of pieces of set information.

* * * * *